(12) United States Patent
Huang et al.

(10) Patent No.: US 6,446,883 B1
(45) Date of Patent: Sep. 10, 2002

(54) NEBULIZER

(75) Inventors: Min Huang; Atsumu Hirabayashi, both of Kodaira (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 09/651,132

(22) Filed: Aug. 30, 2000

(30) Foreign Application Priority Data

Sep. 6, 1999 (JP) .............................. 11-251225

(51) Int. Cl.[7] ................................. B05B 7/06
(52) U.S. Cl. .................... 239/424.5; 239/424
(58) Field of Search ............ 239/424.5, 424, 239/423, 418, 429

(56) References Cited

U.S. PATENT DOCUMENTS 4,977,785 A * 12/1990 Willoughby et al. ......... 239/86
5,513,798 A 5/1996 Tavor

FOREIGN PATENT DOCUMENTS

| JP | 6-238211 | 8/1994 |
| JP | 7-306193 | 11/1995 |
| JP | 8-99051 | 4/1996 |
| JP | 9-239298 | 9/1997 |

OTHER PUBLICATIONS

M. Huang et al, "Microliter Sample Introduction Technique for Microwave–Induced Plasma Mass Spectrometry", Analytical Chemistry, vol. 71, No. 2, Jan. 15, 1999, pp. 427–432.
D. D. Smith et al, "Measurement of Aerosol Transport Efficiency in Atomic Spectrometry", Analytical Chemistry, vol. 54, 1982, pp. 533–537.
S. Augagneur et al, "Determination of Rare Earth Elements in Wine by Inductively Coupled Plasma Mass Spectrometry Using a Nebulizer", Journal of Analytical Atomic Spectrometry, vol. 11, 1996, pp. 713–721.

* cited by examiner

Primary Examiner—Lesley D. Morris
(74) Attorney, Agent, or Firm—Mattingly, Stanger & Malur, P.C.

(57) ABSTRACT

Disclosed herein is a nebulizer capable of performing spraying over a wide flow-rate range from a low flow rate to a high flow rate stably and with high efficiency. Further, the present invention provides a supersonic nebulizer capable of improving the efficiency of spraying by a supersonic region spray gas, and a supersonic array nebulizer wherein a plurality of spray units are placed in array form.

4 Claims, 23 Drawing Sheets

NEBULIZER

BACKGROUND OF THE INVENTION

1. Field of the Invention

The present invention relates to a nebulizer for spraying a liquid with high efficiency, and particularly to a nebulizer suitable for use in an inductively coupled plasma/mass spectrometry system (ICP-MS), an inductively coupled plasma (ICP) atomic emission spectrometry system and an atomic absorption spectrometry system used for inorganic substance analysis.

2. Description of the Related Art

In analytical apparatuses for inductively coupled plasma-mass spectrometry (ICP-MS), inductively coupled plasma atomic emission spectrometry (ICP-AES), etc., aerosol is produced from a solution sample by a nebulizer and introduced into a plasma. Here, substances to be analyzed are brought into atomization, excitation and ionization. Owing to a mass analysis for the resultant ions or a spectrometric analysis for light emitted from excited atoms or ions, the identification and determination of each substance to be analyzed present in the liquid sample are realized. A concentric glass nebulizer is often used as the nebulizer. A description related to ICP-AES is disclosed in, for example, Analytical Chemistry, 54(1982), p.533–p.537. At an end of each spray tube, atmospheric pressure becomes less than or equal to 1 atom. by a spray gas. A difference in pressure between the two ends of the tubes is used so that the liquid sample is sucked into the nebulizer from a container. The flow rate of the gas is 1.0 L/min. and the flow rate of the liquid is about 1.0 mL/min.

A micro concentric nebulizer (MCN) related to ICP-MS has been described in Journal of Analytical Atomic Spectrometry, 11(1996), p.713–p.720. A liquid sample is delivered to a single capillary and sprayed around its end by gas which passes therethrough. The flow rate of the gas is about 1.0 L/min. Since the velocity of the gas is faster than that for the concentric glass nebulizer, the efficiency of its spraying is relatively high. However, the introduced flow rate of a sample solution for realizing high-efficiency spraying is limited. The efficiency of the spraying is reduced when the flow rate thereof is 50 $\mu$L/min or more.

There is need to prevent deposition of a metal due to heat generated upon cutting work, polishing, etc. Thus, a description related to a spray-like body supply device intended for cooling has been disclosed in Japanese Patent Application Laid-Open No. Hei 8-99051. If a liquid is produced or formed in spray form, then cooling can be carried out more effectively. The device has capillaries through which the liquid flows, and an injection hole (nozzle) from which a spray gas (air) is discharged. The cooling liquid is divided into a plurality of the capillaries, and the ends of the plurality of capillaries are packed into a bundle. The liquid is sprayed at the ends thereof by an air flow discharged through one injection hole. The nozzle is shaped in tapered form.

Japanese Patent Application Laid-Open No. Hei 7-306193 describes a sonic spray ionization technology. A quartz capillary (whose inner and outer diameters are 0.1 mm and 0.2 mm respectively) in which a liquid is introduced, has an end inserted into an orifice (whose inner diameter is 0.4 mm). A high-pressure nitrogen gas introduced inside an ion source is discharged into the air through the orifice, and the liquid is sprayed by a sonic gas flow formed at this time. Gaseous ions are produced in aerosol produced by the spraying. In the present ionizing method, the production of fine droplets by the sonic gas flow essentially plays an important role. The liquid in the sonic gas flow is torn off by a gas flow fast in velocity to thereby produce droplets. The non-uniformity of the concentrations of positive and negative ions in droplets firstly produced by spraying becomes pronounced as the size of each droplet becomes fine. Further, some of the liquid are separated from the surface of the droplet by a gas flow, whereby charged fine droplets are produced. Such fine droplets are evaporated in a short time so that gaseous ions are produced. While the size of each produced droplet decreases with an increase in the velocity of flow of gas, the droplet size increases as the velocity of flow of gas enters a supersonic region. This is because a shock wave is produced in the case of the supersonic flow, and the production of fine droplets is depressed. Therefore, according to the sonic spray ionizing method, when the gas flow is sonic, the finest droplets are produced and the produced amount of ions reaches the maximum. The present method discloses that when the flow rate of the spray gas is 3 L/min., a sonic gas flow is formed.

A sonic spray nebulizer has been described in Analytical Chemistry, 71(1999), p.427–p.432. The nebulizer is similar in structure to the ion source for sonic spray ionization. The inner diameter of a resin orifice is 0.25 mm and a quartz capillary (whose inner and outer diameters are 0.05 mm and 0.15 mm respectively) is used. Since a sonic gas flow is used in a spray gas, the present nebulizer is capable of producing extremely fine droplets. As a result, the spray efficiency of a liquid is greatly improved as compared with the conventional glass nebulizer. In the sonic spray nebulizer, the flow rate of the gas is fixed to the condition for the generation of the sonic gas flow, and the flow rate of a liquid sample is controlled by a pump. The flow rate of the gas ranges from 1.0 L/min. to 1.4 L/min., and the flow rate of the liquid ranges from 1 $\mu$L/min. to 90 $\mu$L/min.

On the other hand, a nebulizer using a supersonic gas flow has been described in Japanese Patent Application Laid-Open No. Hei 6-238211 and U.S. Pat. No. 5,513,798. The present nebulizer is characterized in that a supersonic gas flow is helically produced in the neighborhood of a liquid outlet at an end of a capillary by a helical gas path. Further, a cylindrical path is placed on the downstream side from an orifice unit and a shock wave of a supersonic gas flow is repeatedly reflected by the inner surface of the path. Since the shock wave collides with a liquid flow many times in an in-path central portion, droplets are efficiently produced from the liquid cut to pieces. The length (corresponding to the distance between the end of the capillary and the surface of the cylindrical path, which is brought into contact with the air) is as about twice as the diameter of the cylindrical path. The flow rate of gas ranges from 50 L/min. to 60 L/min., and the flow rate of the liquid ranges from 91 mL/min. to 100 mL/min. Since the spray gas helically circles round, the formation of a gas flow concentrically with the capillary as described in the prior art is not carried out. The velocity of flow of the spray gas is divided or resolved into a horizontal direction and a vertical direction with respect to the axis of the capillary. While the velocity of flow of the gas is supersonic, a flow velocity component horizontal to the capillary axis is considered to be less than or equal to the speed of sound. In a droplet producing process, the application of the shock wave to the liquid is important and no emphasis is placed on the tearing off of the liquid by a high-speed gas flow.

Upon vaporization of the liquid, the flow rate of fully-vaporizable water per gas flow rate 1 L/min. is about 20 $\mu$L/min. at most if calculated from saturated vapor pressure at 20° C. Therefore, if sample solution given at a flow rate of 20 μL/min. or more is introduced into an ideal nebulizer when the flow rate of the gas is about 1 L/min., then the efficiency of its spraying should have been reduced in the ideal nebulizer. However, an actual nebulizer shows a tendency to improve analytical sensitivity even if the sample flow rate is 20 μL/min. or more. This is because the spray efficiency of the liquid is considered not to have reached an ideal level.

In the concentric glass nebulizer, the flow rate of the liquid is about 500 μL/min. when the liquid is automatically sucked. Therefore, the full vaporization of liquid cannot be carried out when the flow rate is a gas flow of about 1 L/min. Since a gas flow path is narrow and long structurally, the gas introduced into the nebulizer suffers a pronounced pressure loss in the neighborhood of a jet or injection port or outlet. As a result, the flow velocity of the spray gas is much slower than the speed of sound and the size of each produced droplet is about 10 μm. Most of droplets produced by spraying are coagulated or condensed, whereby they are released from aerosol so as to return to the liquid. Therefore, the spray efficiency of the liquid become extremely low and reaches 1% to 3%. Further, the nebulizer is capable of suitably setting the flow rate of a sample solution through the use of a pump. However, a problem arises in that when the flow rate of the sample solution to be introduced is 300 μL/min. or less, the spraying becomes unstable and hence the nebulizer cannot be used. Therefore, the nebulizer cannot be coupled or linked to a semi-micro liquid chromataographor (liquid flow rate of about 200 μL/min.). (An elementary analytical apparatus might be used to perform a chemical speciation analysis as well as an elementary analysis. In this case, a sample liquid is separated according to the semi-micro liquid chromatography and the separated liquid is introduced into the nebulizer). Even if the flow rate of the liquid sample is increased in a range from 400 μL/min. to 1000 μL/min., the sensitivity of the analytical apparatus little increases. This shows that the substantial amount of the sample introduced into a plasma does not increase.

The micro concentric nebulizer is different from the concentric glass nebulizer, and reduces the flow rate of the liquid sample and improves the efficiency of its spraying. This is because the flow velocity of the gas is considered to be high as compared with the concentric glass nebulizer. Therefore, the micro concentric nebulizer is characterized in that a liquid sample available by a small quantity can be analyzed. However, the flow rate of a liquid sample, which allows the maintenance of high spray efficiency, is less than or equal to 50 μL/min. When the flow rate thereof is greater than that, the sensitivity of the analytical apparatus little increases. As a result, the micro concentric nebulizer is accompanied by a problem in that when liquid samples identical in concentration are analyzed, the sensitivity of the analytical apparatus is low as compared with the use of the concentric glass nebulizer. A problem arises in that particularly when a chemical speciation analysis which uses a semi-micro liquid chromatograph jointly, is performed, the flow rate of a liquid reaches about 200 μL/min. and the sensitivity of the analytical apparatus is insufficient.

The sonic spray nebulizer has a problem similar to the micro concentric nebulizer. While the present sonic spray nebulizer is a nebulizer capable of introducing a liquid given at a low flow rate with high efficiency, it uses a sonic gas flow for the purpose of liquid spraying. Since a wide gas flow path is provided therein, a pressure loss of gas is very low and the sonic gas flow can easily be formed. Further, since the end of a capillary in which the liquid is introduced, is placed in the center of an orifice used as a gas jet port or outlet, the efficiency of spraying is extremely high. However, the flow rate of a liquid sample, which allows the implementation of high spray efficiency, is about 60 μL/min. or less in the sonic spray nebulizer in a manner similar to the micro concentric nebulizer. When the flow rate is greater than that, the spray efficiency is reduced and the sensitivity of an analytical apparatus does not increase significantly.

As described above, the liquid is sprayed through the use of the high-speed (sonic) gas flow in the concentric glass nebulizer, the micro concentric nebulizer, and the sonic spray nebulizer. These nebulizers are respectively accompanied by a problem in that while spraying is carried out through the single jet or injection port or outlet, the spray efficiency is reduced with an increase in flow rate when the liquid flow rate is greater than or equal to about 60 μL/min. When they are installed in a plasma mass analyzer or a plasma atomic emission spectrometry system, it is necessary to properly use nebulizers such as a glass nebulizer, etc. according to the flow rate of the liquid sample, thus causing inconvenience. Particularly when the chemical speciation analysis is done which uses jointly a semi-micro liquid chromatograph in which the liquid flow rate is about 200 μL/min., a problem arises in that, for example, the spraying becomes unstable, thereby making each nebulizer incapable of use, and the spray efficiency becomes low.

As indicated by the sonic spray ionization technology, the size of each produced droplet depends on the gas flow rate. When the flow rate of the spray gas is sufficiently high, the spray efficiency reaches the maximum in the case of the sonic gas flow owing to the effects of tearing off the liquid by the sonic gas flow, and hence the spray efficiency of the liquid becomes high. Japanese Patent Application Laid-Open No. Hei 9-239298 discloses that when a gas flow rate is 3 L/min., a sonic gas flow is formed. Thus, when no limitation is imposed on the gas flow rate relative to the liquid flow rate, the size of each of droplets produced by spraying reaches the minimum upon the speed of sound, and hence droplets each having a sub-micron size of about 0.7 μm are produced in large quantities. When a gas flow slightly faster than the speed of sound is used, the size of each droplet actually tends to increase on the average, but droplets of sub-micron sizes are produced. However, a limitation is often imposed on the flow rate of a usable spray gas in an actually-used nebulizer. In the plasma atomic emission or mass spectrometry system, for example, the flow rate of the spray gas is required to set to about 1 L/min. A restriction is imposed on the gas flow rate relative to the liquid flow rate in order to increase the spray efficiency of a liquid to the maximum under the condition that the gas flow rate is kept constant. As a result, the size of each droplet reaches the minimum where a supersonic gas flow other than the sonic gas flow is formed. This is because even if a shock wave for restraining or controlling the scale-down of each droplet is formed, the production of fine droplets by a gas-flow tearing-off effect becomes effective if a gas flow faster than the speed of sound is formed. Namely, it is desirable that the velocity of flow of the gas is supersonic rather than sonic or less in order to produce droplets each having a sub-micron size in large quantities at a constant gas flow rate and increase the spray efficiency of the liquid to the maximum.

In the nebulizer described in U.S. Pat. No. 5,513,798 which aims to spray a large quantity of liquid in a large quantity of gas, a supersonic spray gas flow is used. In the present nebulizer, the gas flow is not formed concentrically with the capillary as described in the prior art, and the spray gas helically circles round. Droplets of 2 μm to 10 μm are produced by applying a shock wave to the liquid without using the effects of tearing off the liquid by a high-speed gas flow. Since each droplet is large and micron in size, it is difficult to implement an increase in the sensitivity of each system even if the present nebulizer is used as nebulizers for a spectrometry system and a measuring system. Further, since the helical gas flow is formed, the gas flow path is structurally narrow and complex, and the pressure of gas introduced into the nebulizer reaches significant high pressure. A problem arises in terms of fabrication upon applying such a nebulizer to the case where the gas flow is low. While the gas flow rate is set to 1 L/min. in the nebulizers for the ICP atomic emission spectrometry system and the ICP-MS in particular, it is extremely difficult to fabricate a nebulizer which copes with such a low gas flow rate. This is because the gas flow path needs high-accuracy micro-fabrication for the purpose of forming the helical gas flow. A problem arises in that since the high-pressure gas is used, a gas supply means as well as the nebulizer also needs to have high pressure resistance.

In the nebulizer described in Japanese Patent Application Laid-Open No. Hei 8-99051, the introduced liquid is divided into the large number of capillaries. The ends of the large number of capillaries are packed into the bundle, and the liquid is sprayed by the gas flow discharged from one jet or injection port or outlet. However, the capillaries lying in the center of the bundle are hard to contact the gas flow, and the spray efficiency becomes relatively low. The structure of the nozzle shaped in tapered form suffers a noticeable pressure loss, and a high-speed gas flow is hard to occur.

In the conventional nebulizers as described above up to now, the sufficient spray efficiency was not always obtained and a limitation was imposed on an applicable liquid flow-rate range from the viewpoint of the production of the droplets of sub-micron sizes in large quantities.

SUMMARY OF THE INVENTION

An object of the present invention is to provide nebulizer with high spray efficiency, which is capable of producing droplets of sub-micron sizes in large quantities from a wide range of liquid flow rates under a limited gas flow rate.

In order to solve the above problems, the present invention provides a nebulizer which effectively makes use of the momentum of a gas flow for purposes of liquid spraying by using a supersonic spray gas flow lying in the axial direction of a capillary (flow path). Further, the present invention provides a nebulizer provided with a plurality of spray units.

How to increase an opportunity to allow a spray gas and a liquid to collide with each other in a limited time or space is of extreme importance upon spraying the liquid using a compressed gas. Therefore, a solution and gas are uniformly distributed to each individual spray units to thereby make it possible to increase the probability of contact between the solution and the gas.

When the limited spray gas is distributed to the respective spray units, the flow rate thereof is greatly reduced. In order to improve the effects of making collision between the spray gas and the liquid, a supersonic gas flow having much momentum as compared with a sonic gas flow is used. As a result, fine droplets can be produced with satisfactory efficiency.

DESCRIPTION OF THE PREFERRED EMBODIMENTS

Preferred embodiments of the present invention will hereinafter be described in detail with reference to the accompanying drawings.

Embodiment 1

Figure 1:
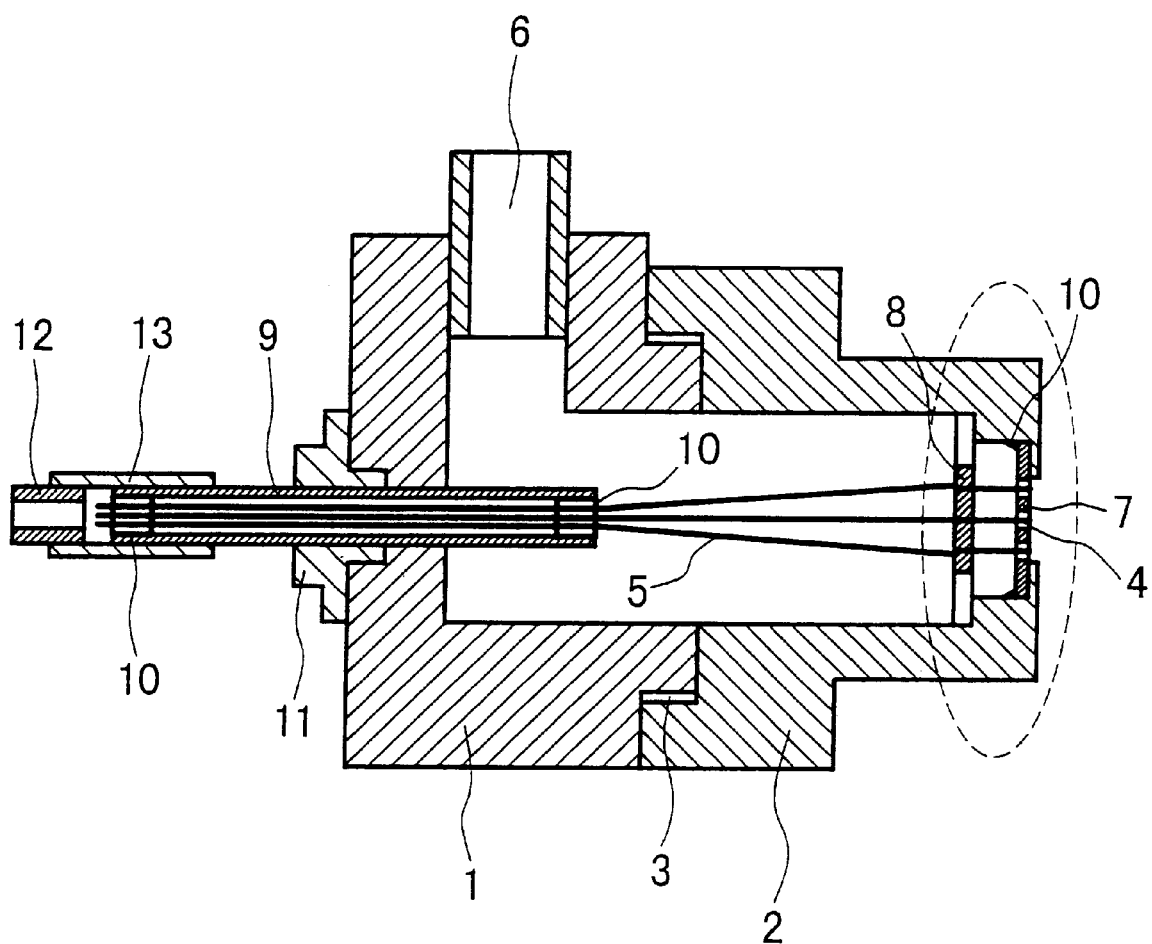
FIG. 1 is a cross-sectional illustration of the supersonic array nebulizer.
Figure 2:
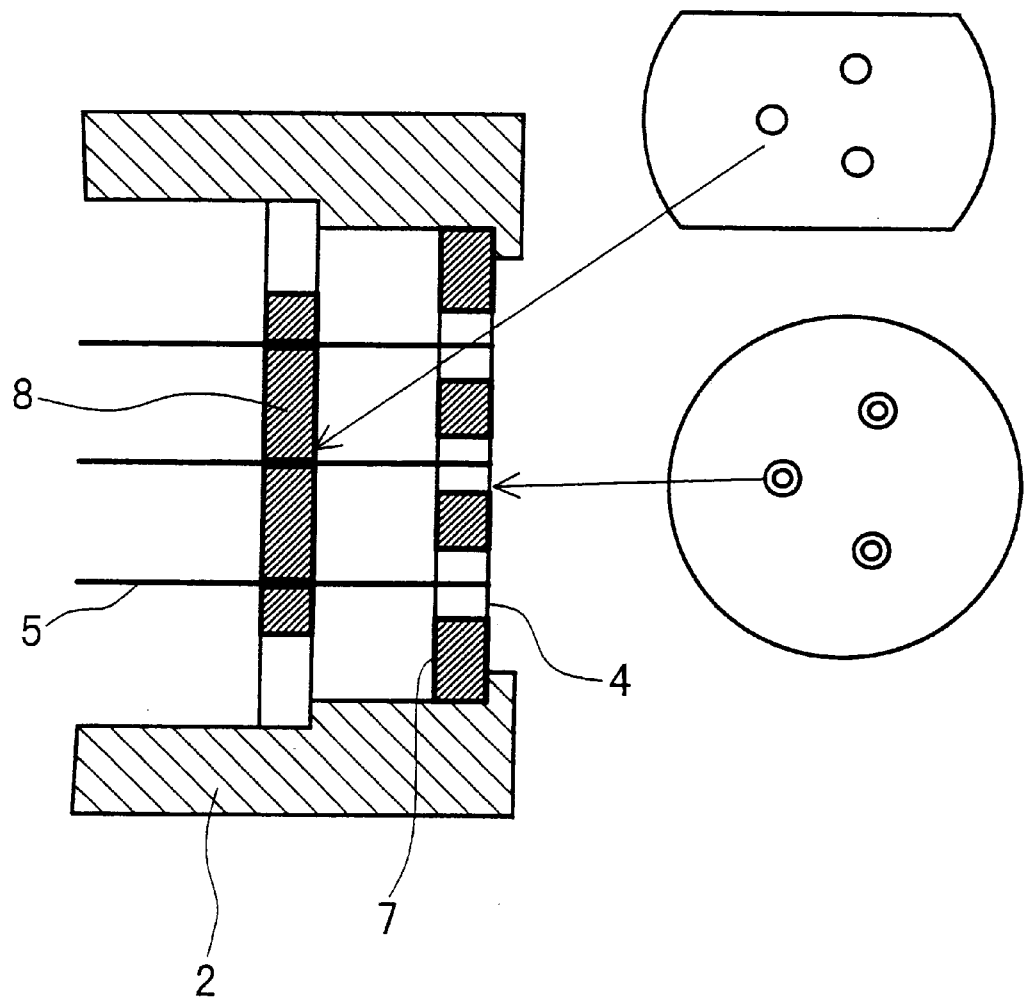
FIG. 2 is an enlarged illustration of part of the nebulizer in FIG. 1.
Figure 3:
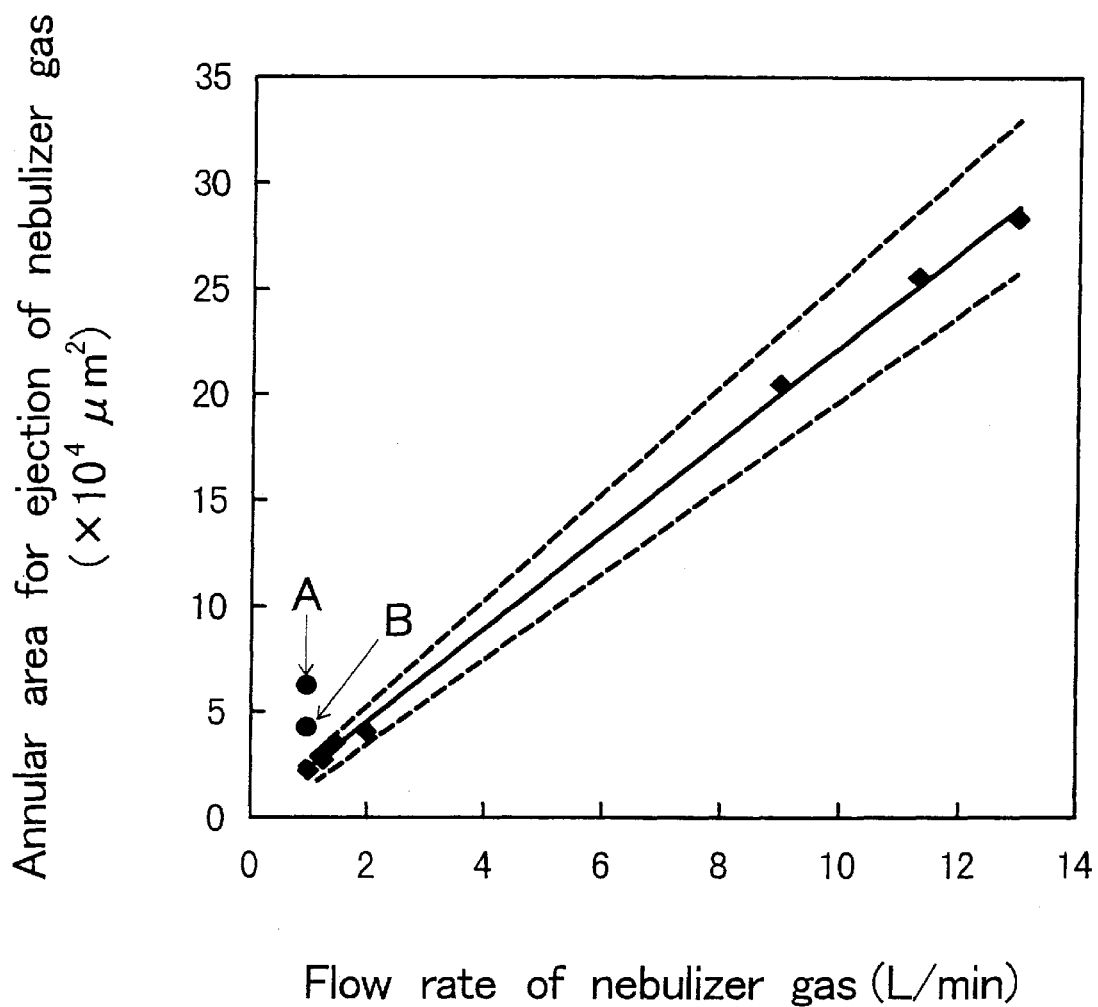
FIG. 3 is relationship between the flow rate of nebulizer gas and the annular area for ejection of nebulizer gas.
Figure 23:
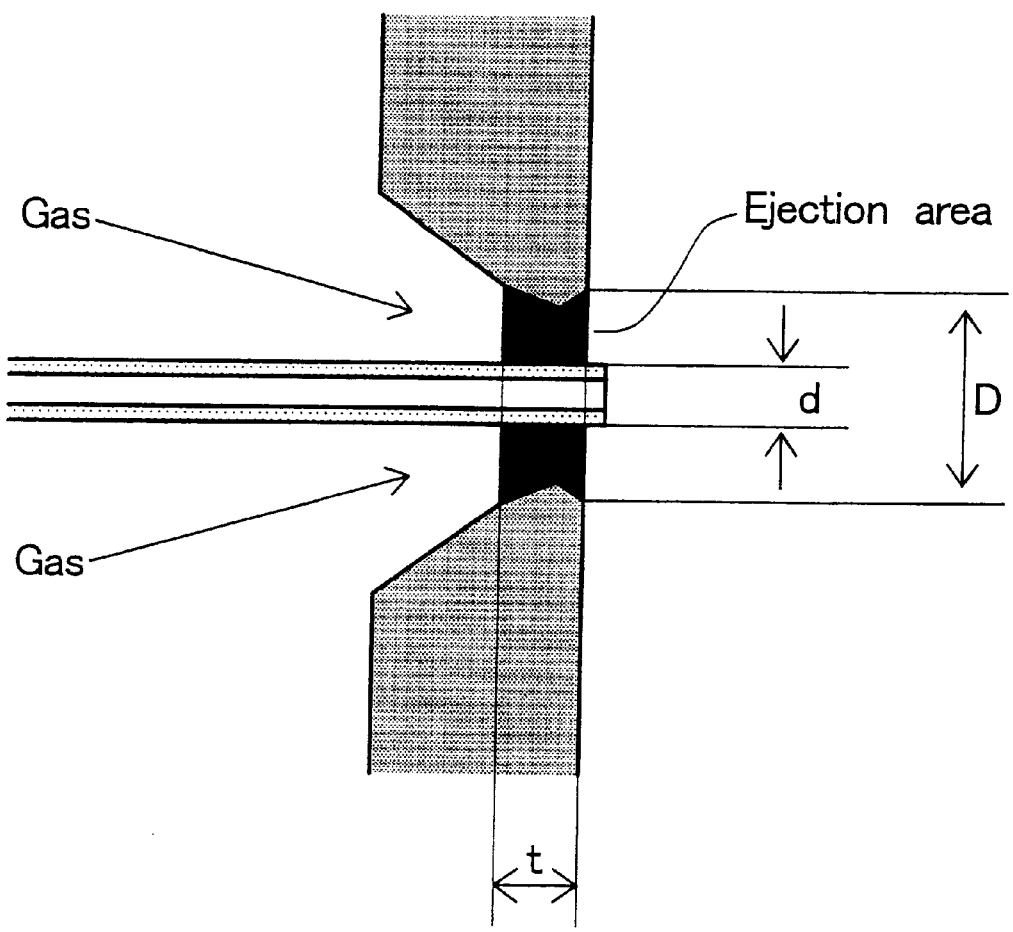
FIG. 23 is a pictorial illustration of part of the nebulizer for gas ejection.

FIG. 1 is a cross-sectional view of a supersonic array nebulizer based on one embodiment of the present invention. FIG. 2 is an enlarged view of orifices shown in FIG. 1. The present supersonic array nebulizer is characterized in that it sprays a supersonic region gas and has a plurality of spray units. Each of the spray units comprises an orifice 4 through which a spray gas or pressurized gas is discharged, and a tube (capillary) 5 through which a sample liquid is introduced. The supersonic region spray gas is injected or delivered through a clearance (jet outlet or tip) defined between the orifice 4 and the tube 5. The liquid sample is divided into several spray units and simultaneously sprayed. Since the flow rate of the liquid sample introduced into each individual units is reduced as compared with the single spray unit, high-efficiency spraying is implemented as a whole. A liquid flow-rate range, which allows the implementation of the high-efficiency spraying, is enlarged.

The supersonic array nebulizer is formed by connecting a first member 1 to a second member 2 with a screw 3. A terminal or end portion of each tube 5 into which the sample liquid is introduced, is inserted into each orifice 4. The end portion of each tube 5 is placed on substantially the same surface as the outside of the orifice 4. A gas supplied from a gas supply means is introduced through a gas inlet 6 and delivered from the orifice 4 to thereby spray the liquid. Each tube 5 is fixed by a fixing plate placed on the upstream side of an orifice member 7. In order to introduce the spray gas into the orifice member 7, the fixing plate 8 is provided with gas pass-through portions. Further, the tube 5 is fixed to a fixing tube 9 with an adhesive 10 to thereby prevent the leakage of the spray gas to the outside of the nebulizer and the leakage of a liquid solution through a gap or clearance defined between the tube 5 and the tube 9. Since a gas flow path is wide inside the nebulizer using the first member 1 and the second member 2, a loss of gas pressure is little produced between the gas supply means and the orifice 4. When the pressure of the gas supplied from the gas supply means is 5 atmospheric pressures, the pressure inside the nebulizer becomes 4.8 atmospheric pressures. The thickness of the orifice member 7 is normally less than or equal to 1.5 mm. In the structure referred to above, a supersonic region gas flow can be formed through the orifice member 7 if the pressure of a gas source is set to about 4 to 5 atmospheric pressures. It is considered in such a nebulizer that the effect of tearing off the liquid by a high-speed gas flow acts effectively and droplets of sub-micron sizes can be produced in large quantities.

In FIG. 1, the reference numbers 11, 12, and 13, respectively, show a connection fitting, a tube for sample solution delivery and a connecting tube.

The flow rate of a spray gas applied to a plasma atomic emission analytical system normally ranges from 0.5 L/min. through 1.5 L/min. and is placed under severe limitations. It is desirable that when consideration is given to the saturated vapor pressure of water, the velocity of flow of a gas falls within a supersonic region when the ratio between the flow rate of a liquid and the flow rate of the gas is greater than $5\times10^{-5}$. A larger quantity of energy can be used for liquid spraying and hence the efficiency of spraying can be improved.

The velocity of flow of the spray gas discharged from the orifice depends on gas pressure on the upstream side of the orifice, the thickness of the orifice member, etc. When the thickness of the orifice member is negligible, the velocity of flow of the spray gas reaches substantially the velocity of sound (Mach 1) when the gas pressure on the upstream side of the orifice reaches 1.9 atmospheric pressures. When the gas pressure reaches 7.8 atmospheric pressures, a supersonic flow of Mach 2 is formed. However, when the thickness of the orifice member is greater than or equal to 2 mm, a pressure loss of the gas at the orifice member is significantly produced. Thus, no sonic gas flow is formed unless the gas pressure on the upstream side of the orifice is set to an extremely high pressure. Higher pressure is required to form the supersonic flow. A gas supply unit such as a regulator of a commonly-used gas cylinder is set to a gas pressure corresponding to about 5 atmospheric pressures at most. Therefore, the thickness of the orifice may desirably be 1.5 mm or less. On the other hand, a problem arises in that when the thickness of the orifice member is less than or equal to 0.1 mm, it breaks from the viewpoint of strength. It is therefore desirable that the thickness of the orifice member ranges from 0.1 mm to 1.5 mm. In the present embodiment, the thickness of the orifice member was set to 0.2 mm and the gas pressure at the gas supply unit was set to 5 atmospheric pressures.

The spray gas is injected through the clearance (space) between the orifice and the tube. The volume (corresponding to annular sectional area x thickness of orifice member) of a space shown in FIG. 23 is important for the purpose of forming the supersonic gas flow. It is desirable that a space volume per spray-gas flow rate equivalent to 1 L/min. is set within a range from $3.6\times10^6$ to $5.1\times10^6$ $\mu m^3$ in each spray unit. When the space volume is less than or equal to $3.6\times10^6$ $\mu m^3$, the supersonic gas flow cannot be formed unless a gas pressure of 7 atmospheric pressures or higher is applied. It is therefore necessary to form devices around the nebulizer as high-pressure resistant and sturdy ones. Thus, the entire system is brought into large size and high cost. On the other hand, when the gas pressure is less than or equal to 7 atmospheric pressures, the generation of a supersonic gas flow having a flow velocity of Mach 2 or more is actually impossible in principle. Therefore, the gas pressure may desirably be used within a range from 1.9 to 7 atmospheric pressures, and the velocity of the generated gas flow falls within a range of Mach 1 to 2.

On the other hand, when the space volume is greater than or equal to $5.1\times10^6$ $\mu m^3$, the flow velocity of the gas is lowered and hence no gas reaches the supersonic region. In a nebulizer employed in a commonly-used plasma mass analytical apparatus or plasma atomic emission analytical apparatus, the flow rate of a gas normally ranges from 0.5 L/min. to 1.4 L/min. It is therefore necessary to set the total volume defined between the tube and the orifice to a range from $1.8\times10^6$ to $7.1\times10^6$ $\mu m^3$. Incidentally, the length of the orifice at a portion where the tube and the orifice are closest to each other, may be set to the thickness of the orifice member upon estimating the volume. In the present embodiment, the orifice member comprises a plate having a thickness of 0.2 mm.

An evaluation was performed in a state in which when the thickness t of the orifice member is less than or equal to 1.5 mm, a nebulizer utilizing orifices and tubes of various sizes in combination, was fabricated and installed in an analytical apparatus. The flow rate of a gas introduced into the nebulizer was kept substantially constant. The result thereof is collectively shown in FIG. 3. An annular sectional area in FIG. 3 corresponds to an annular sectional area of a gas flow in a region in which the tube and the orifice are closest to each other. The annular sectional area=$\{\pi(D^2-d^2)/4\}$ is calculated by using a diameter D of each orifice and a diameter d of each tube. There may be cases where the processing of the orifice is done by a drill and it is performed by the application of a laser beam or by etching. Therefore, the inner diameter of the orifice is not always kept constant depending on processing means or the accuracy of processing in the case of the narrowest region (length t) in which the gas passes through each orifice 4 as shown in FIG. 23. According to the result shown in FIG. 3, the inner diameter of the narrowest portion through which the gas passes, is defined as D, and a region in which the inner diameter is greater than D by about 20%, is included in a region in which the thickness of the orifice member is t. Data obtained from an example illustrative of a nebulizer in which a satisfactory result was not obtained, are respectively indicated as symbols A and B. In the case of A, an area per spray-gas flow rate equivalent to 1 L/min. is $6.2\times10^4$ $\mu m^2$. It was revealed that the size of spray was large and the efficiency of spraying was low. If the area is reduced to $3.5\times10^4$ $\mu m^2$ (above B), then the efficiency of spraying is improved and the size of spray becomes much finer. However, if compared with a result placed below a solid line as a result of the execution of evaluation experiments under the installation of a nebulizer satisfying the condition of B in a plasma emission analyzer, then the sensitivity of its analysis was only the half thereof. If the area per spray-gas flow rate equivalent to 1 L/min. is less than or equal to $2.3\times10^4$ $\mu m^2$, the velocity of the spray gas reaches a supersonic region from the calculation of a slope or inclination of the solid line shown in FIG. 3. It is desirable that since a processing error of about 10% is not often avoided, the annular sectional area is less than or equal to $2.53\times10^4$ $\mu m^2$ for the purpose of bringing the velocity into the supersonic region. It is necessary to set the entire system to a high-pressure resistant and sturdy one when gas pressure capable of being used for the nebulizer reaches a high pressure of 10 atmospheric pressures or higher. It is desirable that if it is taken into consideration, then the area per spray-gas flow rate equivalent to 1L/min. is set to within a range from $1.8\times10^4$ to $2.53\times10^4$ $\mu m^2$.

While a plurality of pieces of tube are used for the supersonic array nebulizer, a problem arises from the practical viewpoint in that there is high possibility that when the inner diameter of each tube 5 is less than or equal to 5 $\mu$m, the tube 5 will be clogged with particles such as dust. If the inner diameter is greater than or equal to 200 $\mu$m, the efficiency of tearing off the liquid lying in the center of each tube by a gas flow is reduced. As a result, the size of each droplet generated from the nebulizer increases and the spray efficiency of the liquid discharged by spraying is degraded. This is because the more the size of each droplet becomes fine, the more the liquid is easy to be vaporized. Therefore, the inner diameter of each tube 5 needs to fall within a range of 5 to 200 $\mu$m in order to obtain the high spray efficiency of the liquid. Further, the spray efficiency of the liquid depends even on the flow rate of the liquid introduced into one tube 5. It is therefore desirable that the flow rate of the liquid per tube 5 is set to less than or equal to 100 $\mu$L/min. Further, the spray efficiency of the liquid discharged by spraying depends on the wall thickness (corresponding to ½ of the difference between the outer diameter and the inner diameter) of each tube 5. The tube thin in thickness is improved in spray efficiency. While, however, a problem normally arises in terms of the strength if the wall thickness does not reach greater than or equal to 5$\mu$, the spray efficiency is significantly reduced when the wall thickness is greater than or equal to 100 $\mu$m. The fixing plate 8 for fixing the position of each tube 5 is disposed at a distance of 1 to 15 mm as viewed from the orifice member 7. If set to greater than or equal to 20 mm, then the vibration of the tube 5 becomes pronounced and exerts a bad influence on spraying. There is a fear that when less than or equal to 1 mm, the fabrication of the nebulizer becomes difficult, and a pressure loss of the nebulizer gas becomes pronounced because the space defined between the fixing plate and each orifice is small.

In the present embodiment, the orifice member 7 is provided with the three orifices. The holes equal to the same number as above are defined in the fixing plate 8. Each tube 5 is a molten silica capillary (flow path) whose outer diameter, inner diameter and length are respectively 127 $\mu$m, 50 $\mu$m and 80 mm. The three orifices 4 whose diameters are 170 $\mu$m, are defined in a disk 7 comprised of a stainless material whose surface having a thickness of 0.2 mm is subjected to corrosion-resistant coating and provided at the apexes of a triangle at 2-mm equal intervals. The distance between each orifice 4 and the fixing plate 8 is 5 mm. A tip or a leading portion or end of the second member is cylindrical and has an outer diameter of 9 mm. The leading end thereof is inserted into a cover provided with a seal O-ring for a spray chamber cover to thereby connect the nebulizer and a spray chamber to each other.

Figure 4:
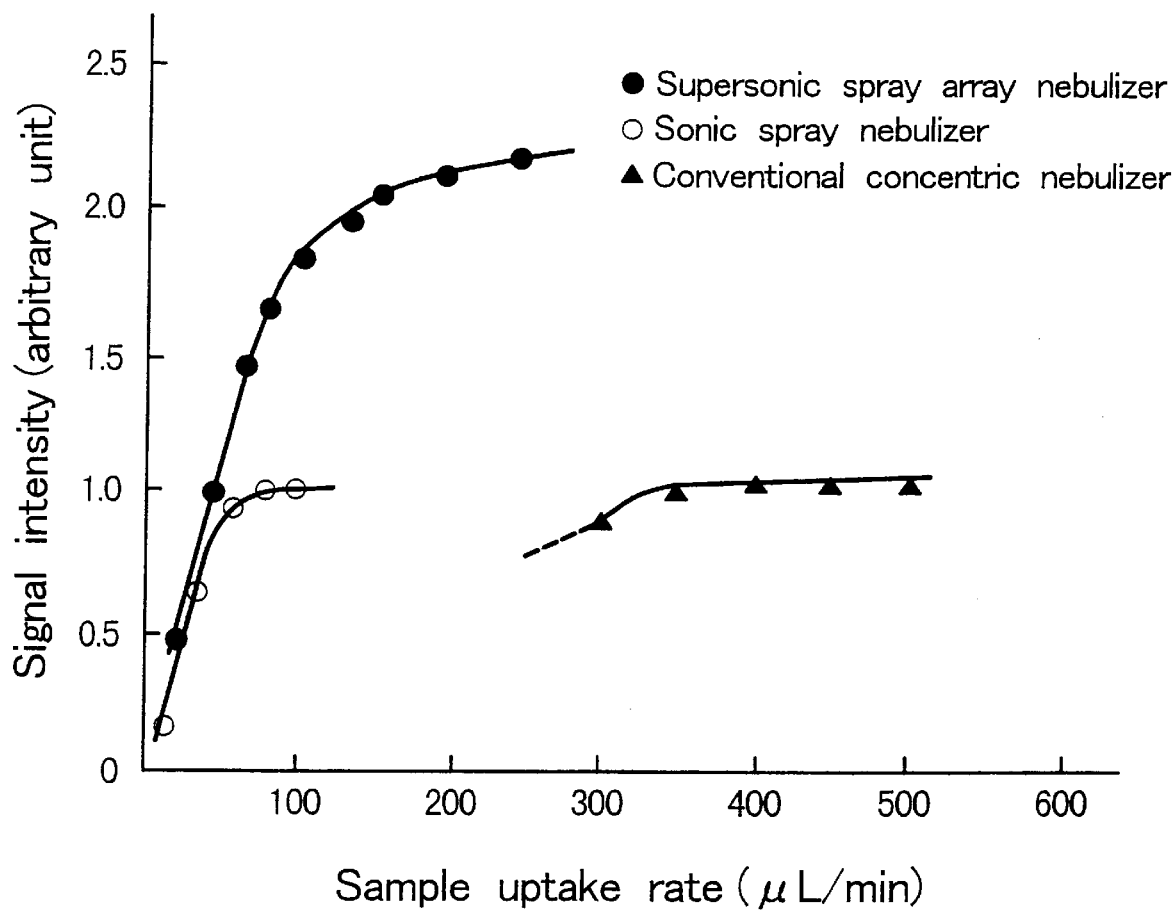
FIG. 4 is comparison of variation of signal intensity at different sample uptake rate for the supersonic spray array nebulizer, the sonic spray nebulizer and the conventional concentric nebulizer.

FIG. 4 shows the dependence of each signal intensity obtained by the plasma atomic emission analytical apparatus on each sample flow rate. If the spray efficiency is constant, then the sample flow rate and the signal intensity should be brought to a proportional relationship. However, since the spray efficiency is reduced as the sample flow rate increases in practice, the proportional relationship tends to disappear. Even if a sample flow rate of a glass concentric nebulizer is increased to 300 to 400 $\mu$L/min., the signal intensity (sensitivity of analytical apparatus) does not increase so far. Particularly when the sample flow rate is 400 $\mu$L/min. or more, the signal intensity little increases. On the other hand, when the sample flow rate is 300 $\mu$L/min. or less, spraying becomes unstable and the analysis thereof becomes difficult. While a sonic spray nebulizer is capable of spraying a sample small in flow rate with high efficiency, the signal intensity of the analytical apparatus little increases when the sample flow rate is greater than or equal to 60 $\mu$L/min. As a result, a problem arises in that a nebulizer usable for a high-sensitivity analysis does not exist in a sample flow-rate range of 100 to 300 $\mu$L/min. as shown in the drawing. When, for example, the flow rate of a liquid in a semi-microcolumn is about 200 $\mu$L/min., and the semi-microcolumn is coupled to the upstream side of the analytical apparatus to perform a chemical speciation analysis, the high-sensitivity analysis is actually difficult. When the supersonic array nebulizer is used, the signal intensity significantly increases till an introduced sample flow rate of 300 $\mu$L/min. As compared with the glass concentric nebulizer, it is shown that when the supersonic array nebulizer is used, the maximum signal intensity can be increased to about twice. As described above, one nebulizer can cope with an extremely small flow rate to a few hundred $\mu$L/min. if the supersonic array nebulizer is used. It has been recognized that when a relative standard deviation (RSD) of each signal intensity is less than or equal to 3%, the analytical apparatus can be used for quantitative analysis. Therefore, a result of stability (RSD) of spraying relative to the liquid flow rate, which has been examined by ten times-continuous measurements, is shown in Table 1. RSD is shown as 2.61 at the maximum with respect to sample flow rates equivalent to 7 to 250 µL/min. This result shows that the nebulizer is sufficiently high in stability within the above flow-rate range and can be used for quantitative analysis.

TABLE 1

Spray Stability (RSD) of Supersonic Array Nebulizer RSD % Element

| Flow rate (µL/min) | Cr | Mn | Co | Cu | As | Se |
|---|---|---|---|---|---|---|
| 7 | 1.43 | 1.13 | 1.74 | 1.35 | 1.90 | 1.25 |
| 20 | 1.84 | 1.53 | 1.96 | 1.28 | 2.52 | 2.61 |
| 30 | 0.20 | 1.00 | 0.87 | 0.42 | 0.44 | 0.20 |
| 60 | 1.43 | 1.13 | 1.74 | 1.35 | 2.25 | 1.25 |
| 80 | 1.97 | 0.52 | 0.96 | 0.38 | 1.04 | 0.44 |
| 100 | 1.03 | 1.55 | 0.83 | 0.54 | 1.55 | 1.82 |
| 150 | 0.43 | 0.19 | 2.09 | 1.43 | 0.40 | 1.67 |
| 200 | 1.77 | 2.03 | 1.09 | 0.16 | 0.98 | 1.43 |
| 250 | 0.72 | 0.88 | 1.15 | 0.72 | 1.24 | 1.47 |

Embodiment 2

Figure 5:
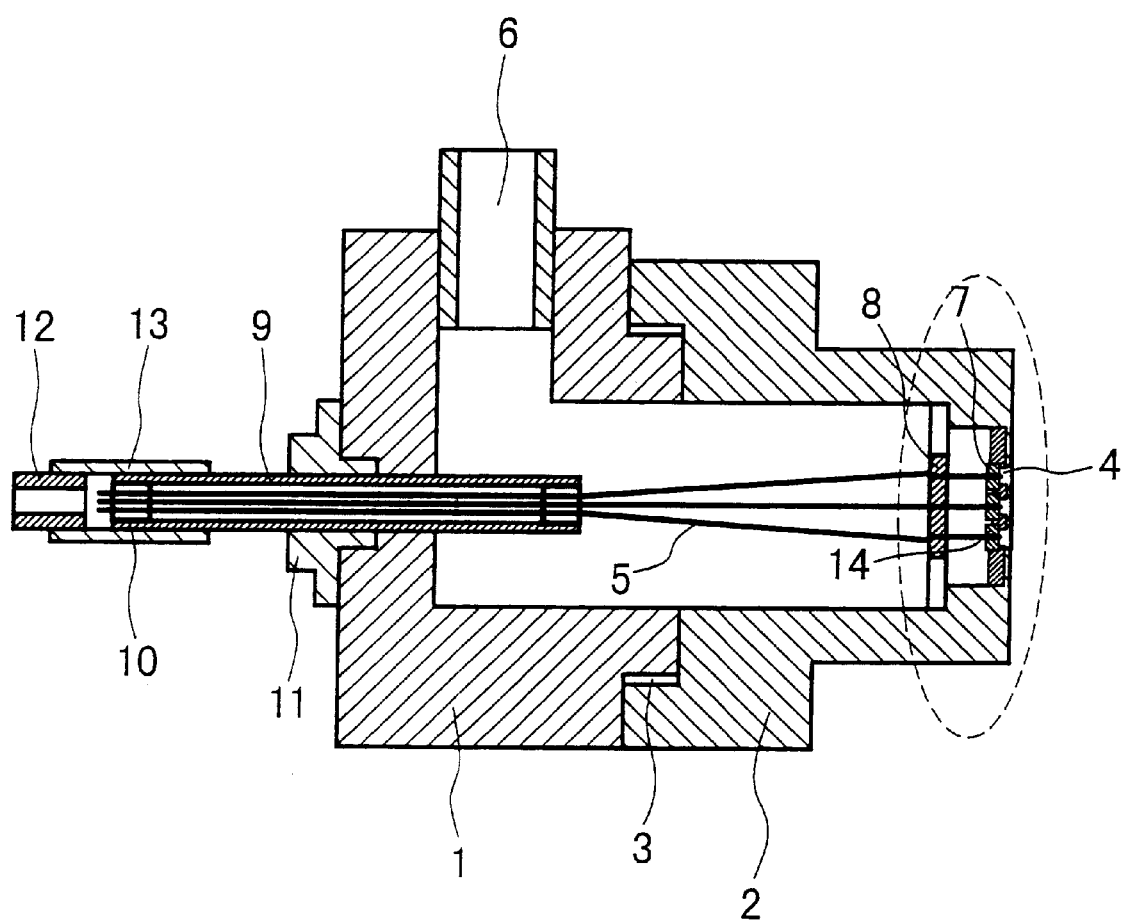
FIG. 5 is a cross-sectional illustration of the supersonic spray array nebulizer with orifices formed by using pieces of resin tube.
Figure 6:
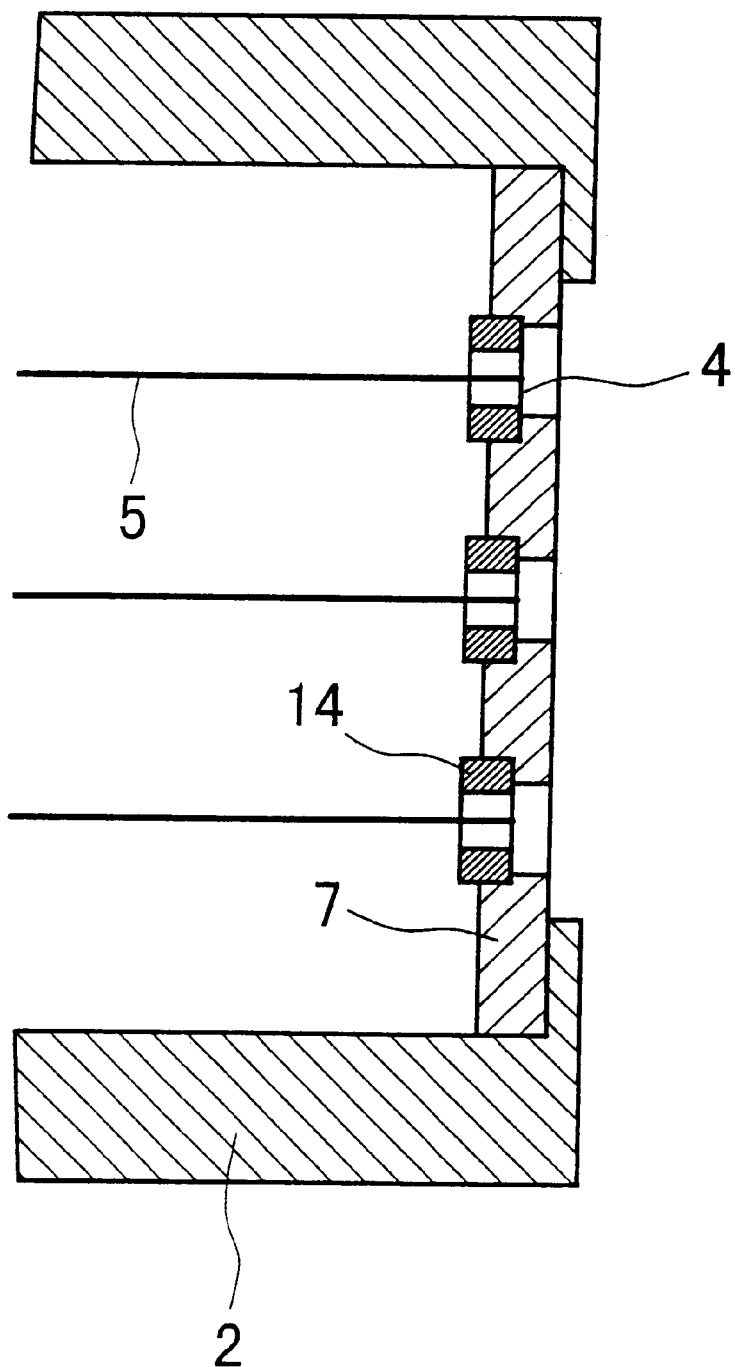
FIG. 6 is an enlarged illustration of part of the nebulizer in FIG. 5.

A schematic diagram of a supersonic array nebulizer based on another embodiment of the present invention is shown (in FIG. 5). While a basic structure is provided as shown in FIG. 1, FIG. 5 shows an example in which each orifice 4 makes use of one obtained by slicing a resin tube. FIG. 6 is an enlarge view of each orifice shown in FIG. 5. A plastic tube identical in inner diameter (e.g., 170 µm) to the orifice 4 is cut with a thickness of 0.5 mm, and disks 14 for the resultant three plastic tubes are respectively fit in three holes defined in a leading end of a second member, which in turn are fixed with an adhesive. This corresponds to an orifice member whose diameter is 170 µm and whose thickness is 0.5 mm. The three orifices are provided at the apexes of a triangle at 4-mm equal intervals.

Embodiment 3

Figure 7:
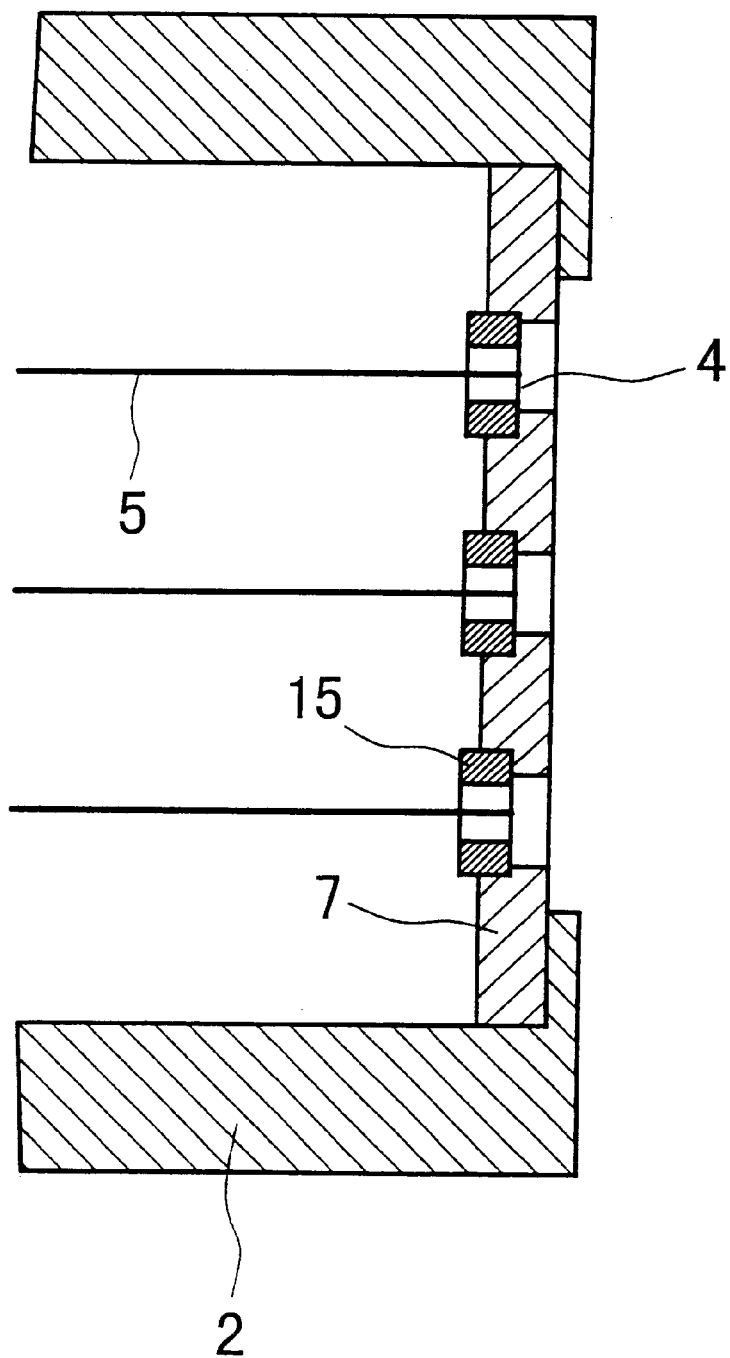
FIG. 7 is an enlarged illustration of the supersonic spray array nebulizer whose orifices are formed on pieces of ceramic material disk.
Figure 8:
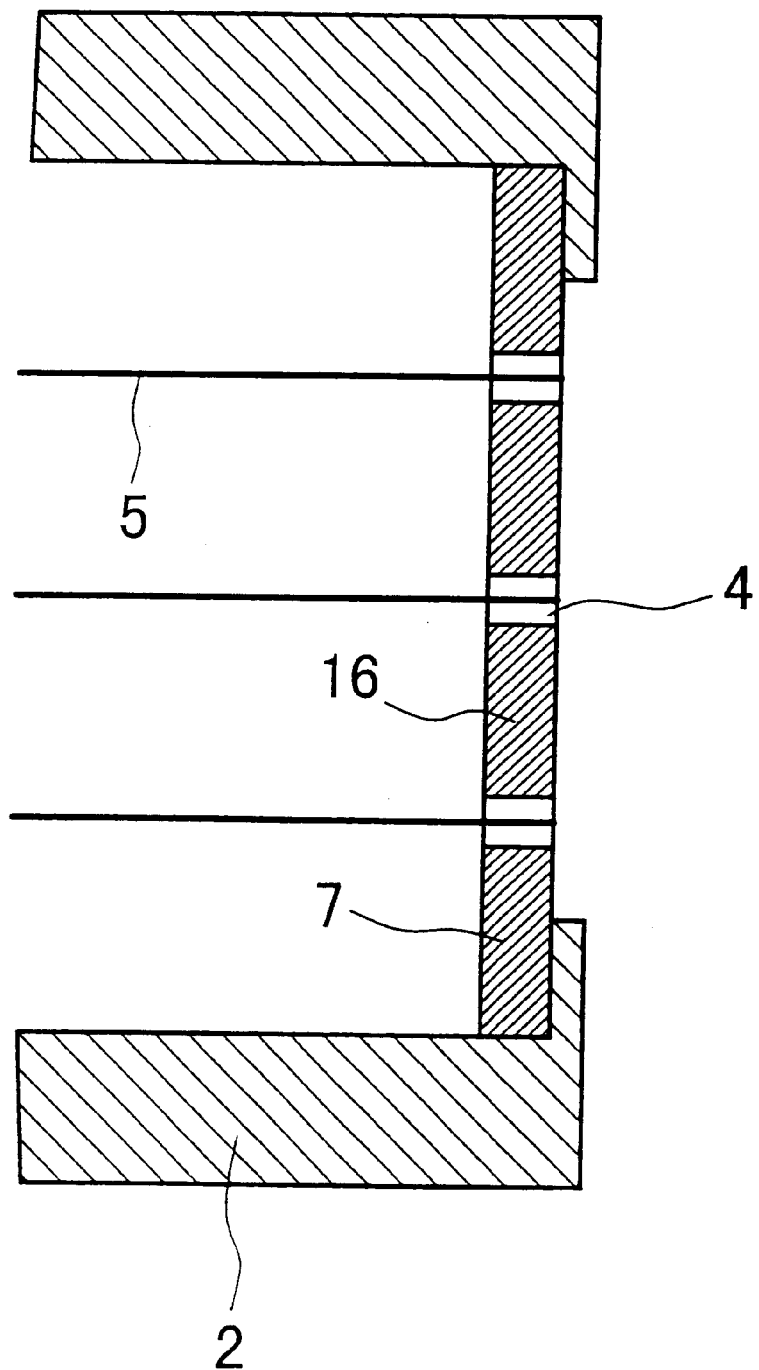
FIG. 8 is an enlarged illustration of the supersonic spray array nebulizer whose orifices are formed on a single piece of ceramic material disk.

FIGS. 7 and 8 are respectively enlarged views of orifices of the supersonic array nebulizer based on another embodiment of the present invention. A basic structure of the nebulizer is similar to the embodiment shown in FIG. 5 but an orifice member 7 is fabricated with a ceramic material. A ruby orifice material 15 (whose diameter and thickness are 2 mm and 0.3 mm respectively) having orifices each having an inner diameter of 170 µm is shown in FIG. 7. Three disks are respectively fixedly fit in three holes defined in a second member. The three orifices are fixed at 4-mm equal intervals. On the other hand, a large ruby orifice member 16 (whose diameter and thickness are 6 mm and 0.3 mm respectively) is shown in FIG. 8.

Embodiment 4

Figure 9:
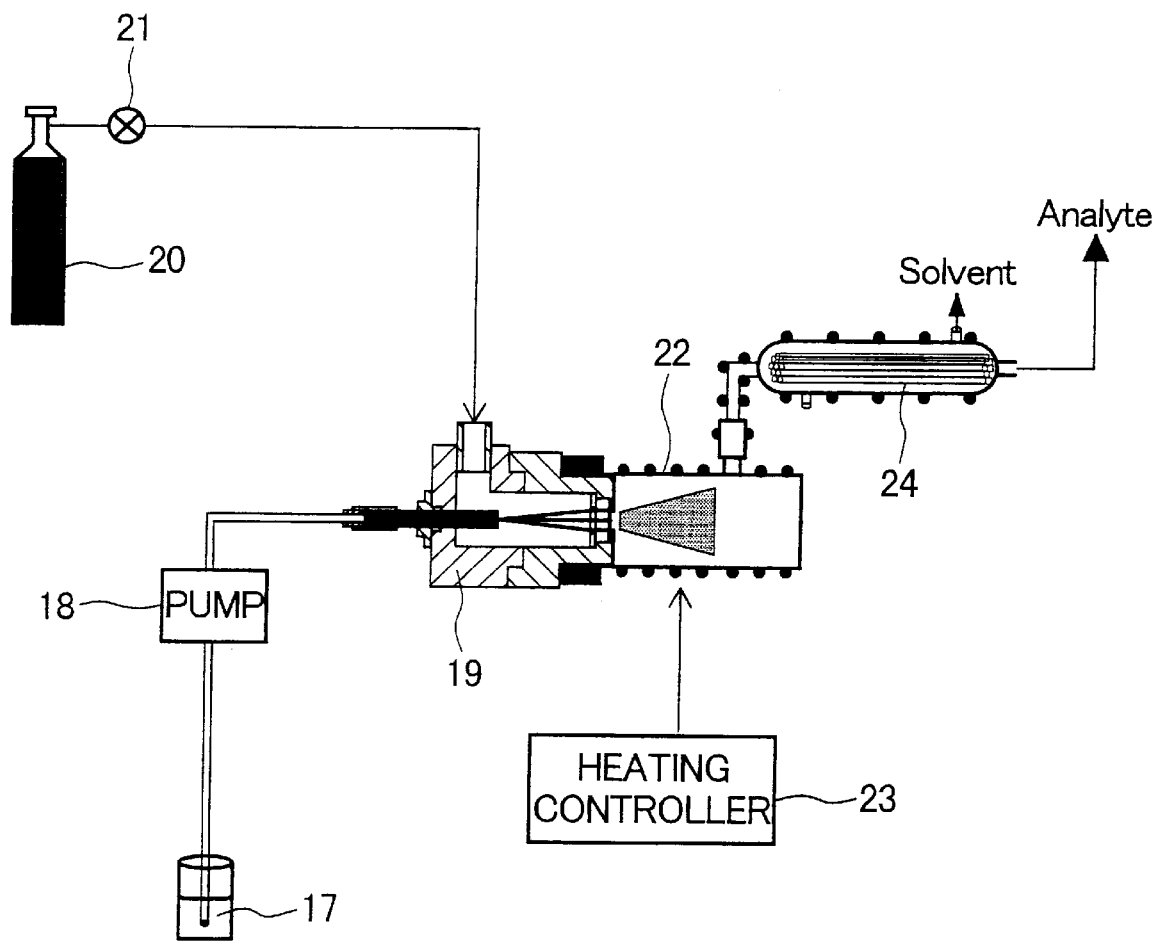
FIG. 9 shows a sample introduction system in which the supersonic spray array nebulizer combines with a membrane separator for solvent removal.
Figure 10:
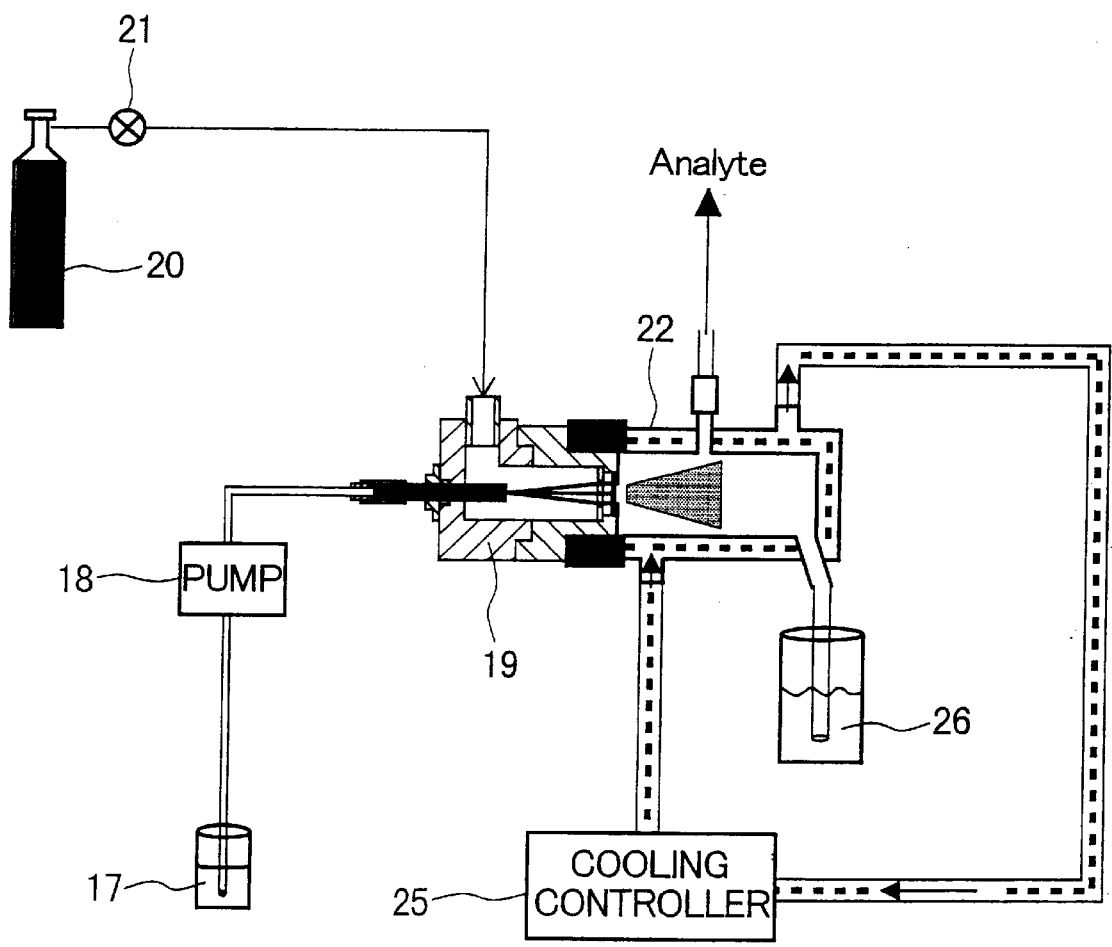
FIG. 10 shows a sample introduction system in which the supersonic spray array nebulizer combines with a cooling device for solvent removal.

In an apparatus for plasma emission analysis and plasma mass analysis, a solution sample is first sprayed by a nebulizer to produce aerosol. Next, the aerosol is introduced into a plasma so as to be brought into atbmization, excitation or ionization, whereby ions or radiation light is analyzed. It is therefore of importance that fine aerosol is produced by the nebulizer and the sample is introduced into the plasma with satisfactory efficiency. Further, the introduction of a large quantity of solvents (molecules) into the plasma might exert a bad influence on the analysis thereof. Thus, there may be cases in which the solvents in the aerosol stand in need of their positive removal. This is because the temperature of the plasma is lowered due to the large quantity of solvents, and the production of molecular ions derived from the solvents and the radiation from solvent molecules cause a reduction in analytical sensitivity. FIGS. 9 and 10 are respectively configurational diagrams of a sample introduction system using the supersonic array nebulizer including a solvent removal process, based on one embodiment of the present invention. A sample solution 17 is introduced into a supersonic array nebulizer 19 by a pump 18. Therefore, the sample solution 17 is controlled to 5 atmospheric pressures by a pressure-reducing valve or regulator 21 and thereby sprayed by an introduced gas. Two types are considered as a method of removing the solvent molecules in the aerosol. In the solvent removing method shown in FIG. 9, the aerosol is heated and thereby evaporated, followed by separation of the solvent through a membrane. In a spray chamber 22 heated to about 150° C., droplets in the aerosol are fully vaporized and introduced into a membrane separator 24. The membrane having the property of allowing only the solvents to pass therethrough is used to thereby remove the solvent molecules which interferes with the analysis. The remaining substances to be analyzed are introduced into the plasma together with a carrier gas, followed by atomization and ionization. On the other hand, in the method shown in FIG. 10, a spray chamber 22 is cooled to −5° C. and subjected to evaporation to capture solvent molecules and droplets by the surface of the spray chamber 22. Owing to this function, the removal of the solvent molecules is implemented.

Embodiment 5

Figure 11:
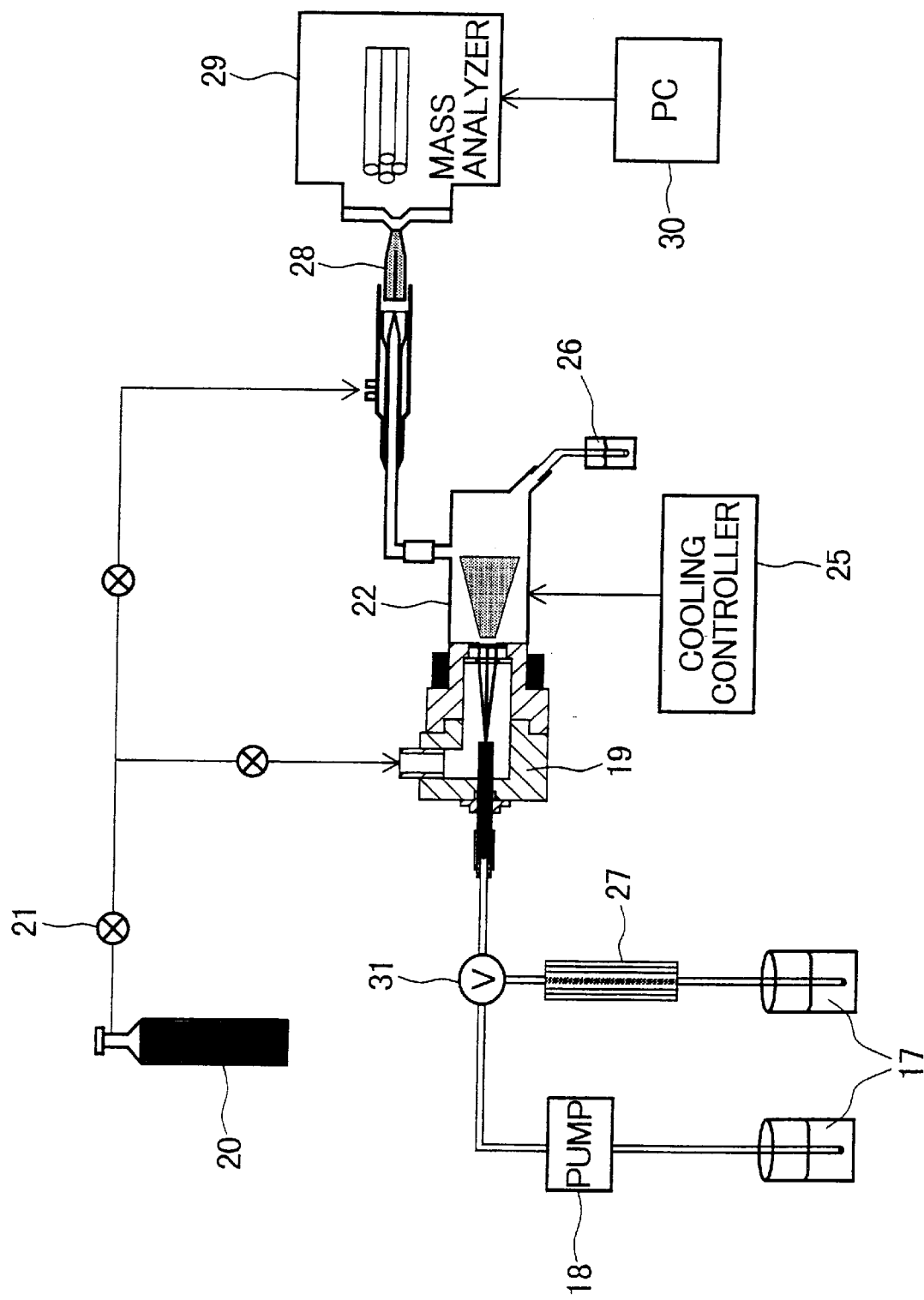
FIG. 11 is a schematic diagram of an inductively coupled plasma mass spectrometry system in which a semi-microcolumn is connected with the supersonic spray array nebulizer.

FIG. 11 is a configurational diagram of an inductively coupled plasma mass spectrometry (ICP-MS) system using the supersonic array nebulizer combined with a semi-microcolumn, based on one embodiment of the present invention. A sample solution 17 is subjected to chemical speciation separation or normal chemical separation and concentration by a semi-microcolumn 27, followed by introduction into a supersonic array nebulizer 19. Therefore, the solution 17 is sprayed from a gas cylinder 20 through the use of a spray gas (4.5 atmospheric pressures) controlled by a pressure-reducing valve or regulator 21. Aerosol produced by spraying is introduced into a cooled spray chamber 22 to thereby remove solvents. Thereafter, the remaining aerosol is introduced into a plasma 28. Analyzed substances ionized by the plasma are fractionated and detected by a mass analyzer 29. The flow rate of the solution in a semi-microcolumn is normally about 200 µL/min. and a concentric glass nebulizer is not capable of coping with it. The use of the supersonic array nebulizer allows the use of the semi-microcolumn. Owing to such a system, a chemical speciation analysis for, e.g., arsenic, selenium, etc. can be performed, and information about the level of toxicity as well as the total volume of elements can also be obtained. The system is expected to be widely applied in, for example, medical and toxicological fields starting with an environmental field. When the separation of the column is not required, a valve 31 is switched to directly introduce the sample solution 17 delivered by a peristaltic pump 18 into the supersonic array nebulizer 19 as shown in FIG. 11. A spray chamber 22 is cooled to −5° C. by a cooling controller 25 to thereby remove solvents. Analytical sensitivity is improved three times as compared with the use of the normally concentric nebulizer in which the sample flow rate is 400 µL/min.

Embodiment 6

Figure 12:
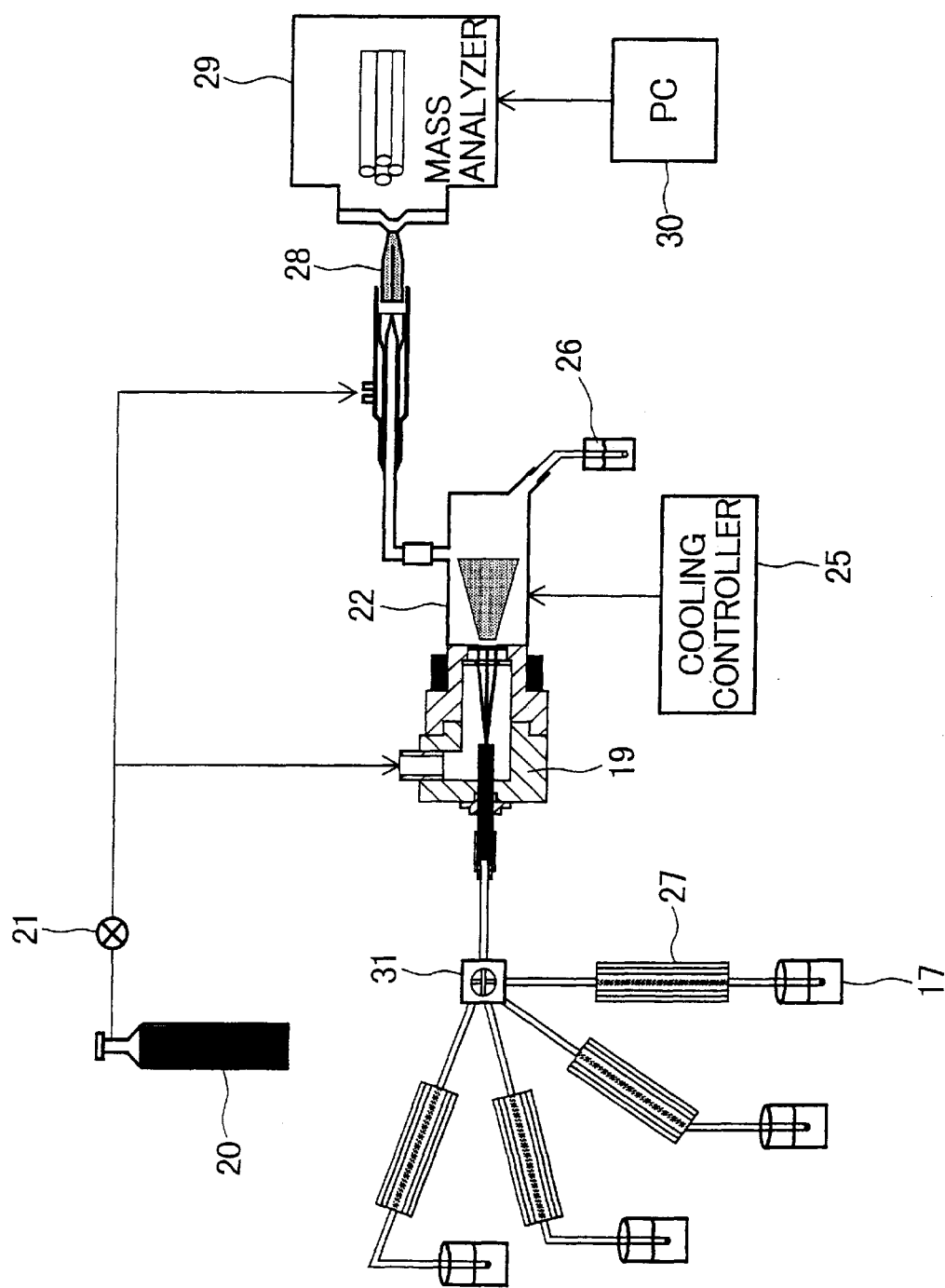
FIG. 12 is a schematic diagram of an analytical instrument system which includes several semi-microcolumns connected with the supersonic spray array nebulizer.

FIG. 12 shows a system in which a large number of semi-microcolumns are coupled to the supersonic array nebulizer based on one embodiment of the present invention. While the separation of the columns normally needs a few minutes to several tens of minutes, the width of the time (bandpeak) required to elute a separated solution is about one minute. Therefore, the simultaneous use of the large number of semi-microcolumns at intervals of several minutes allows the implementation of a high-throughput analysis.

Embodiment 7

Figure 13:
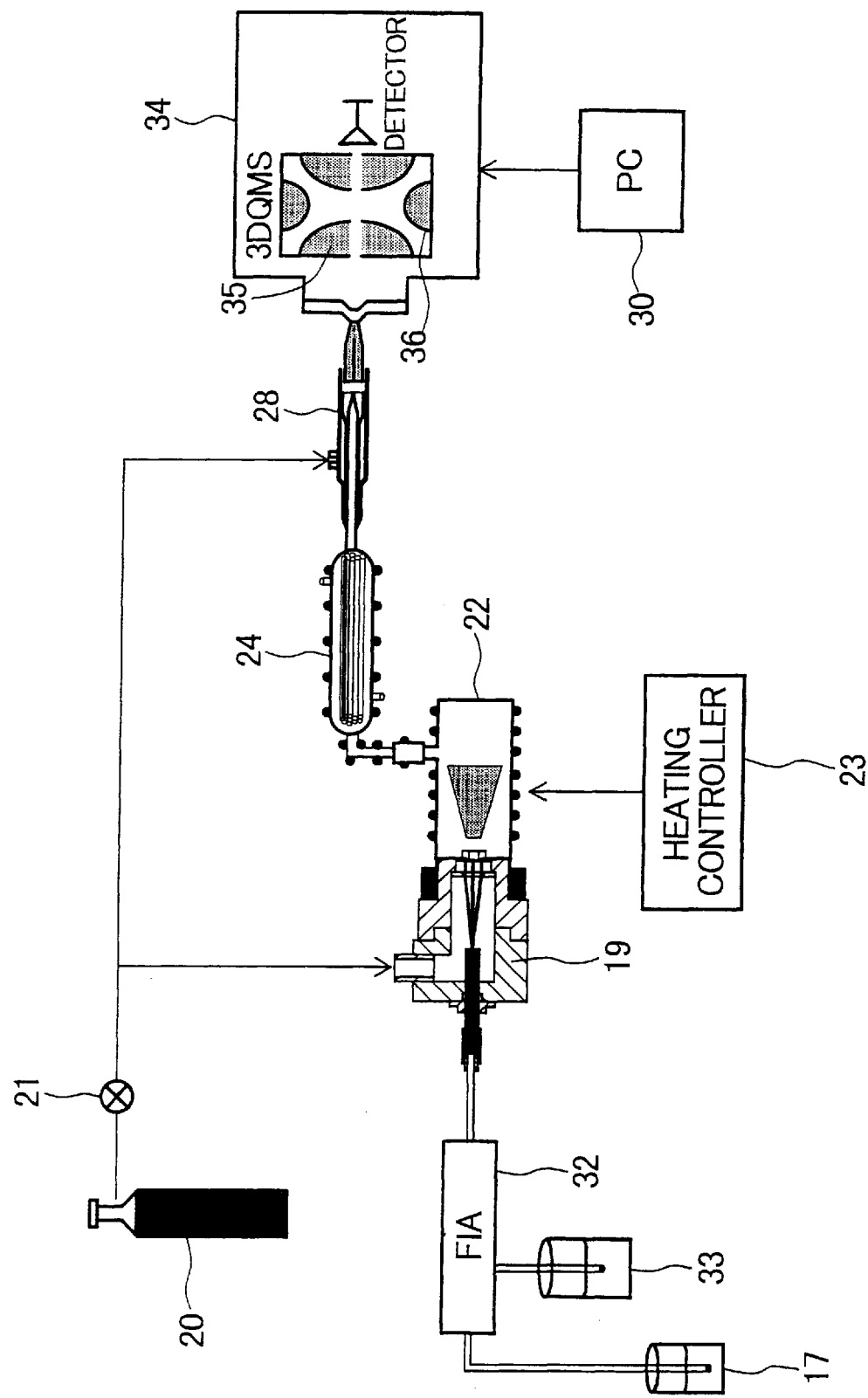
FIG. 13 is a schematic diagram of an inductively coupled plasma mass spectrometry system which employs the supersonic spray array nebulizer combined with a flow injection equipment.

FIG. 13 is a diagram showing an inductively coupled plasma mass spectrometry system using the supersonic array nebulizer based on another embodiment of the present invention. A three dimensional quadrupole (quadrupole ion trap) mass analyzer 34 is used as a mass analytical apparatus. A mass analytical unit comprises a pair of bowl-shaped end cap electrodes 35 and a doughnut-shaped ring electrode 36. When a high-frequency voltage V is applied to the ring electrode, ions each having a specific mass number or more are taken in the electrodes according to the applied voltage. After the completion of capturing of the ions, the high-frequency voltage V is scanned from a low voltage to a high voltage to thereby sequentially un-stabilize the ions from the ions each having a low mass number. Thereafter, the ions are discharged outside the electrodes and detected. The mass number of each ion can be determined according to the relationship between the mass number of each detected ion and V. The determination of the quantity of each ion is implemented based on the detected signal intensity. In the present system, a sample solution 17 and solvent (water) 33 are alternately introduced into a supersonic array nebulizer 19 by a flow injection apparatus 32 and sprayed therefrom. Generated aerosol is introduced into a spray chamber 22. In the spray chamber 22 heated to 150° C. by a heating controller 23, evaporated water molecules are removed by a separation membrane 24 which allows only water vapor to pass therethrough. The remaining substances to be analyzed are introduced into a plasma (ICP) 28 where they are ionized. The produced ions are introduced into the mass analyzer 34. The three dimensional quadrupole (quadrupole ion trap) mass analyzer is capable of dissociating molecular ions and removing different types of ions each having the same mass number. Further, a high-sensitivity analysis is realized owing to analyte enrichment based on the three dimensional quadrupole. When the pressure of a spray gas is 4 atmospheric pressures, the flow rate of the spray gas is 1 L/min., and the flow rate of a sample to be introduced is 250 µL/min., the strength of each detected ion is increased to four times as compared with the use of a glass nebulizer in which the flow rate of the sample to be introduced is 400 µL/min.

Embodiment 8

Figure 14:
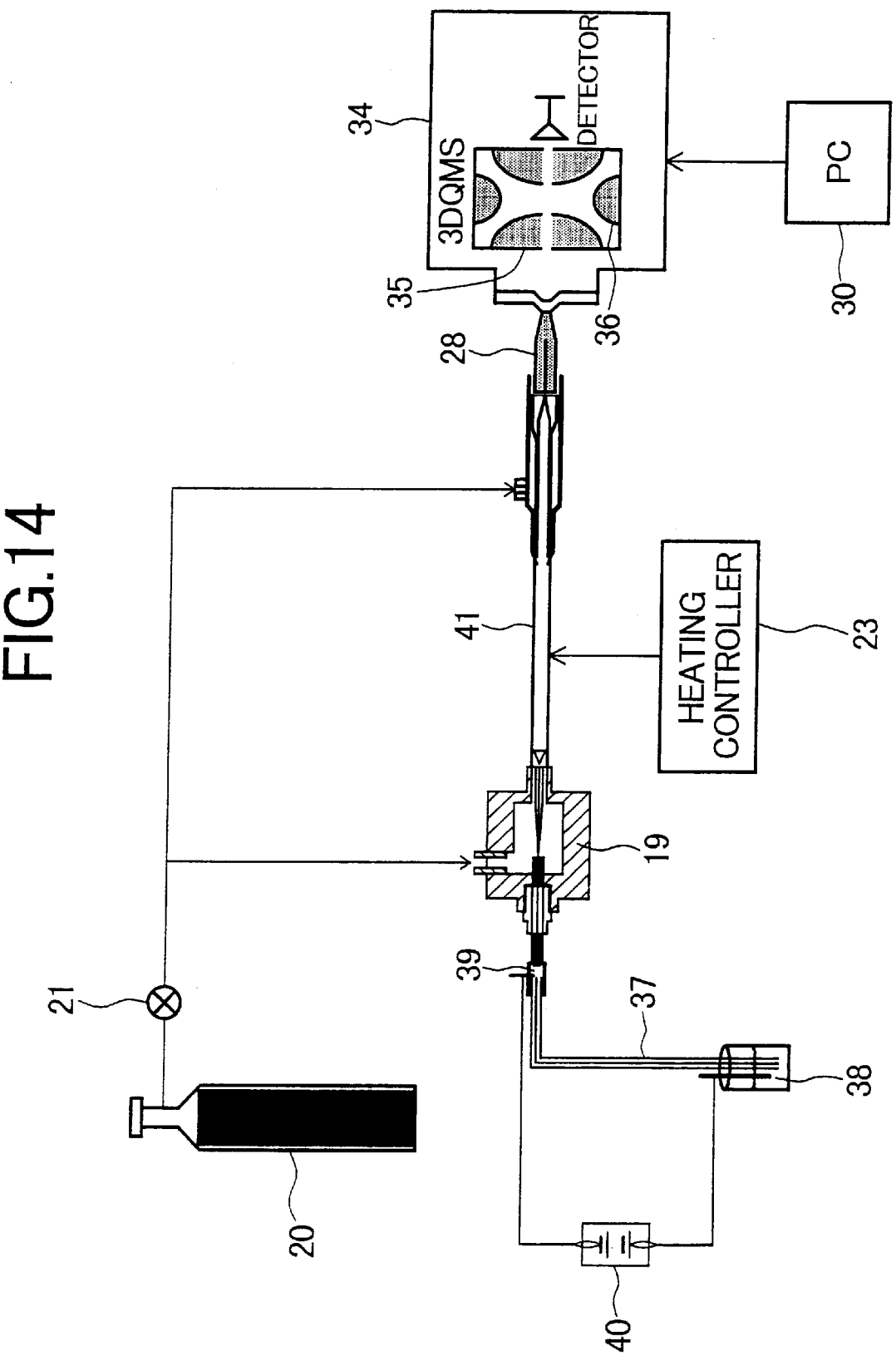
FIG. 14 is a schematic diagram of an inductively coupled plasma mass spectrometry system which employs the supersonic spray array nebulizer combined with an electrophoresis device for chemical speciation analysis.

FIG. 14 is a diagram showing an inductively coupled plasma mass spectrometry system for chemical speciation analysis, which uses the supersonic array nebulizer based on another embodiment of the present invention. The present system separates various chemical speciation substances according to capillary electrophoresis (CE) and detects the same by the ICP-MS. A sample containing $AsO^{2-}$, $AsO^{3-}$, $SeO_3^{2-}$, and $SeO_4^{2-}$ is introduced into three separation capillaries 35 (whose outer and inner diameters are respectively 127 µm and 50 µm) having a length of 30 cm. One end of each capillary 37 is dipped into a buffer solution 38 and the other end thereof is dipped into a conductive auxiliary solution 39. A voltage of 10 to 25 kV is applied between both ends of each capillary by a high-voltage supply device 40 to thereby realize electrophoresis. The separated sample is introduced into a nebulizer 19 from which it is sprayed. In order to prevent a reduction in high resolution obtained by the electrophoresis, aerosol is directly introduced into a plasma 28 through a connecting tube 41 to perform a sample analysis. In an example experimented under the condition that the buffer solution comprises $NaH_2PO_4$ whose concentration is 0.075 mol/L and $Na_2B_4O_7$ (pH 7.65) whose concentration is 0.0025 mol/L, and the applied voltage is 20 kV, the separation and detection of the above components are completed in about 15 minutes since the commencement of the electrophoresis. The limited concentration for their detection is about 0.08 ng/mL.

Embodiment 9

Figure 15:
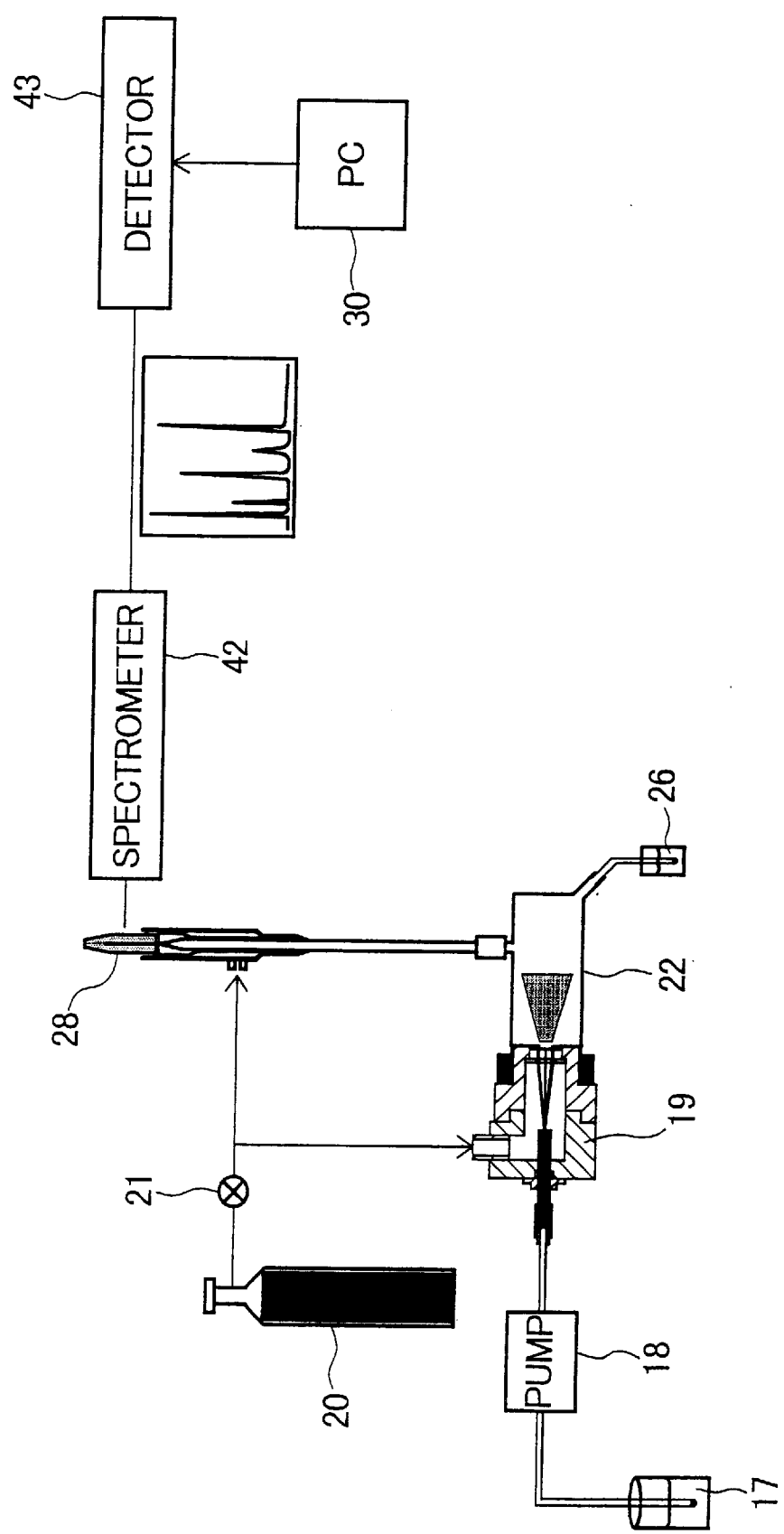
FIG. 15 is a schematic diagram of using the supersonic spray array nebulizer for an inductively coupled plasma atomic emission spectrometry system.

FIG. 15 is a configurational diagram of an inductively coupled plasma atomic emission spectrometry system using the supersonic array nebulizer based on one embodiment of the present invention. A sample solution 17 is introduced into a supersonic array nebulizer 19 by a micro-tube pump 18. An argon spray gas in a gas cylinder 20 is controlled to 4 atmospheric pressures by a pressure-reducing valve or regulator 21 and supplied to the supersonic array nebulizer. A spray chamber 22 removes slightly large droplets contained in aerosol produced by spraying and discharges them into a waste reservoir 26. The remaining aerosol is introduced into a plasma 28. Substances to be analyzed are atomized by the plasma 28, followed by excitation and light-emission. The emitted light is wavelength-separated by a spectrometer 42 and detected by a detector 43. A personal computer 30 performs the control of the system and data processing.

Figure 16:
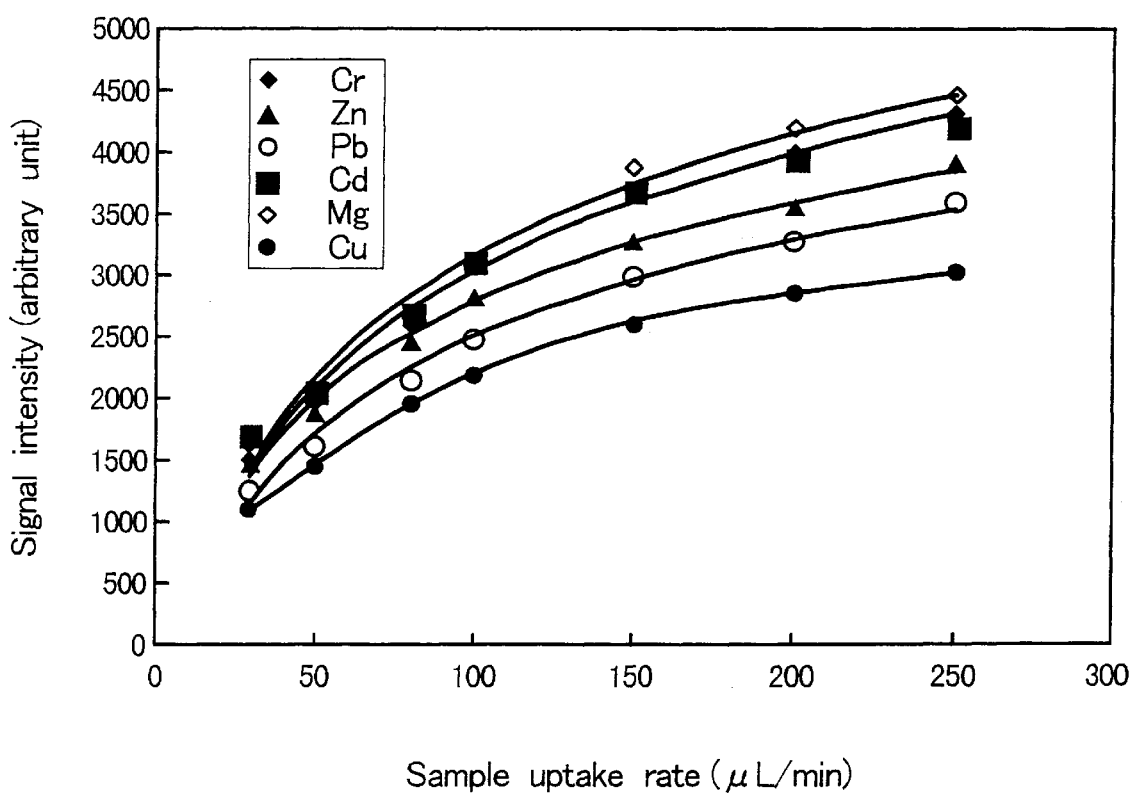
FIG. 16 shows experimental results obtained with the inductively coupled plasma atomic emission spectrometry system which employs the supersonic spray array nebulizer for sample introduction.

A measured result obtained by experiments done under the condition that the pressure of a spray gas is 4.5 atmospheric pressures and the flow rate of the spray gas is 1 L/min., is shown in FIG. 16. When the flow rate is less than or equal to 250 µL/min., the intensity of a signal increases with an increase in sample flow rate. This trend is a characteristic of the supersonic array nebulizer. While the flow rate is greatly reduced as compared with a flow rate (830 µl/min.) at the time of the use of a concentric glass nebulizer, the sensitivity of the analytical apparatus is improved about twice (wavelengths: Sn 189.989 nm; Cr 205.552 nm; Zn 213.856 nm; Pb 220.353 nm; Cd 228.802 nm; Mn 257.61 nm; Mg 279.553 nm; Cu 324.754 nm). It was also revealed that the supersonic array nebulizer was high in stability as well as compared with the glass nebulizer. When the flow rate of the sample to be introduced is 250 µL/min. and the concentration of an analyzed substance in the sample solution is 1 µg/mL, a relative standard deviation (RSD) obtained by ten times-continuous measurements is less than or equal to 1.5%.

Embodiment 10

Figure 17:
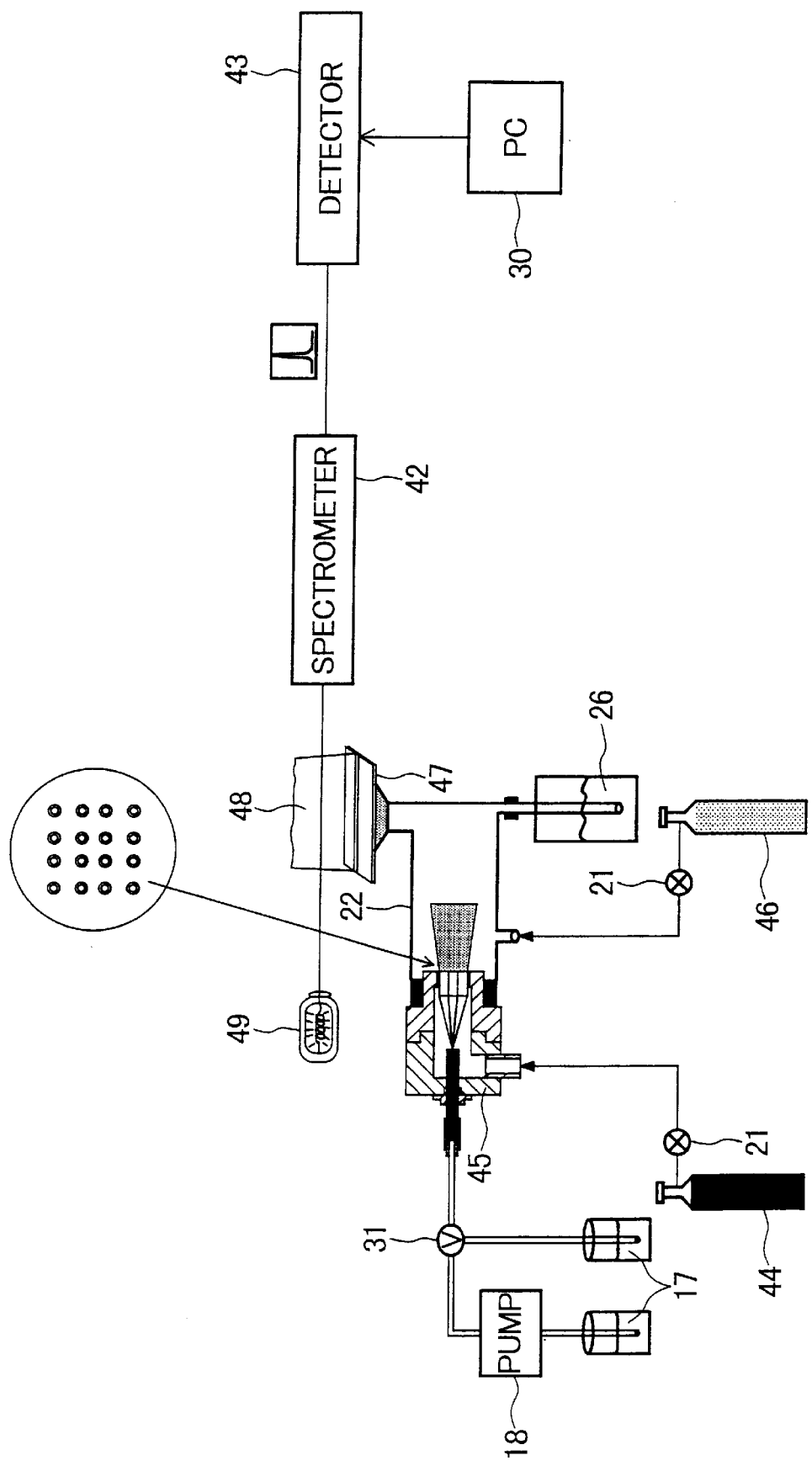
FIG. 17 is a schematic diagram of an atomic absorption spectrometry system which employs the supersonic spray array nebulizer for sample introduction.

FIG. 17 is a configurational diagram of an atomic absorption spectrometry system using the supersonic array nebulizer based on one embodiment of the present invention. In the present example, a supporting gas (air) delivered at several tens of L/min. is used as a spray gas and a solution sample is sprayed therethrough.

As shown in FIG. 17, a spray gas delivered from an air cylinder 44 is depressurized by a pressure-reducing valve or regulator 21 and introduced into a supersonic array nebulizer 45. A sample solution is introduced into the nebulizer 45 by self absorption and distributed to a plurality of tubes (capillaries) whose ends are inserted into plural orifices. The sample solution is sprayed therethrough by supersonic region supporting gas flows generated form the orifices. A spray chamber 22 removes relatively large droplets contained in aerosol and discharges them into a waste reservoir 26. A fuel gas delivered from an acetylene cylinder 46 is mixed with the aerosol within the spray chamber 22 and thereafter burned by a burner 47. In a plasma (acetylene-air flame) 48 exceeding 2000° C., droplets are vaporized and each substance to be analyzed is atomized. A radiation beam emitted from a hollow cathode lamp 49 is applied to the plasma (acetylene-air flame) 48, whereby the absorbance of the atomized substance to be analyzed is measured by a spectrometer 42 and a detector 43. As a means or unit for introducing the sample solution, the introduction of it by a peristaltic pump 18 can also be utilized as well as self absorption. The thickness of an orifice member is 1.5 mm. An array nebulizer comprising 16 molten silica tubes (whose inner and outer diameters are respectively 200 $\mu$m and 100 $\mu$m) and 16 orifices (whose inner diameters are respectively 250 $\mu$m) is mounted to a polarized Zeeman atomic absorption spectrometry system and an evaluation experiment was done in this state. As a result, sensitivity similar to the normal nebulizer was obtained even though the flow rate of a sample fluid was 1 mL/min. (1/5 of the normal flow rate). Further, the analytical sensitivity of the atomic absorption spectrometry system was improved about twice as compared with the normal nebulizer from the result that a sample solution delivered at a flow rate of 5 mL/min. has been introduced by the peristaltic pump 18.

Embodiment 11

Figure 18:
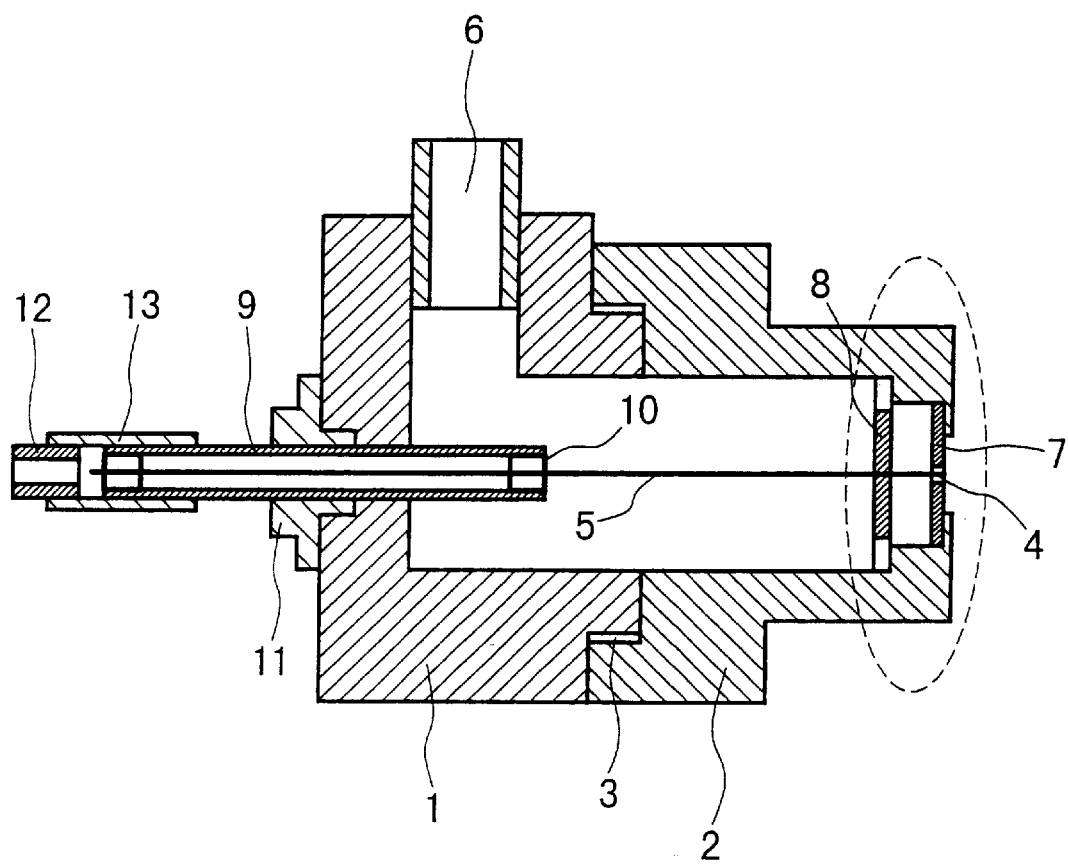
FIG. 18 is a cross-sectional illustration of a supersonic spray nebulizer with a single orifice.
Figure 19:
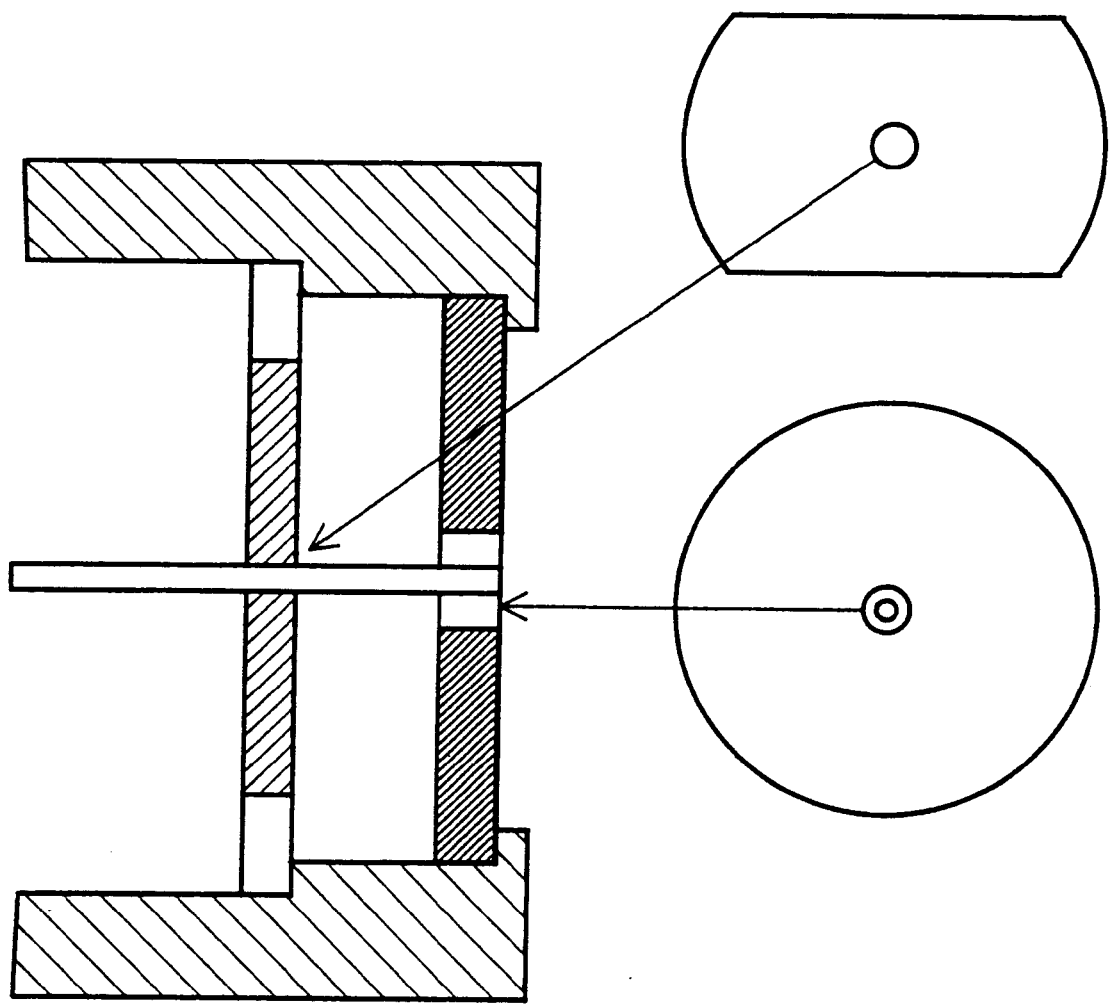
FIG. 19 is an enlarged illustration of part of the nebulizer described in FIG. 18.
Figure 20:
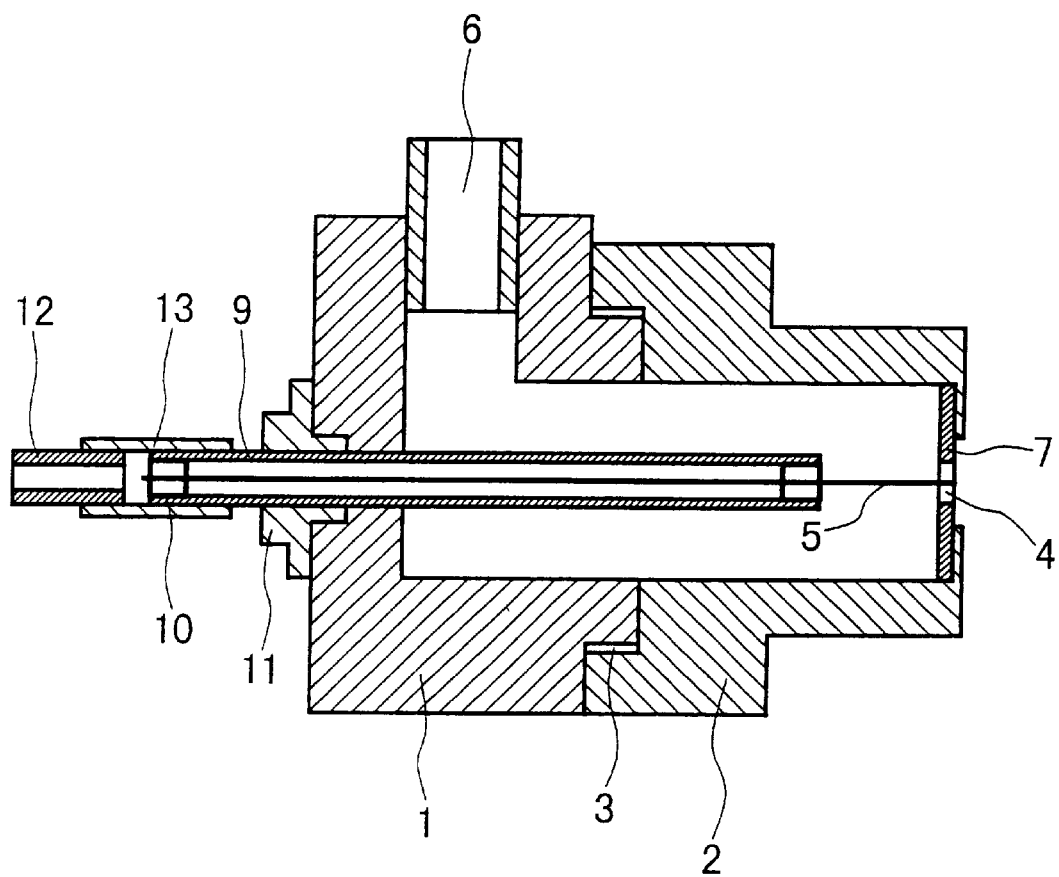
FIG. 20 is a cross-sectional illustration of a single-orifice supersonic spray nebulizer without using a plate to fix the tube.

FIG. 18 is a cross-sectional view of the supersonic nebulizer based on another embodiment of the present invention. While the present supersonic nebulizer is structurally similar to the nebulizer shown in FIG. 1, the number of spray units is one. However, the present nebulizer is also sprayed through a supersonic region gas. FIG. 19 is an enlarged view of an orifice shown in FIG. 18. FIG. 20 is similar to FIG. 18 but no fixing plate is used in FIG. 20. A tube 5 is supported by a fixing tube 9 extended to a position away 5 mm from a spray hole or port.

Embodiment 12

Figure 21:
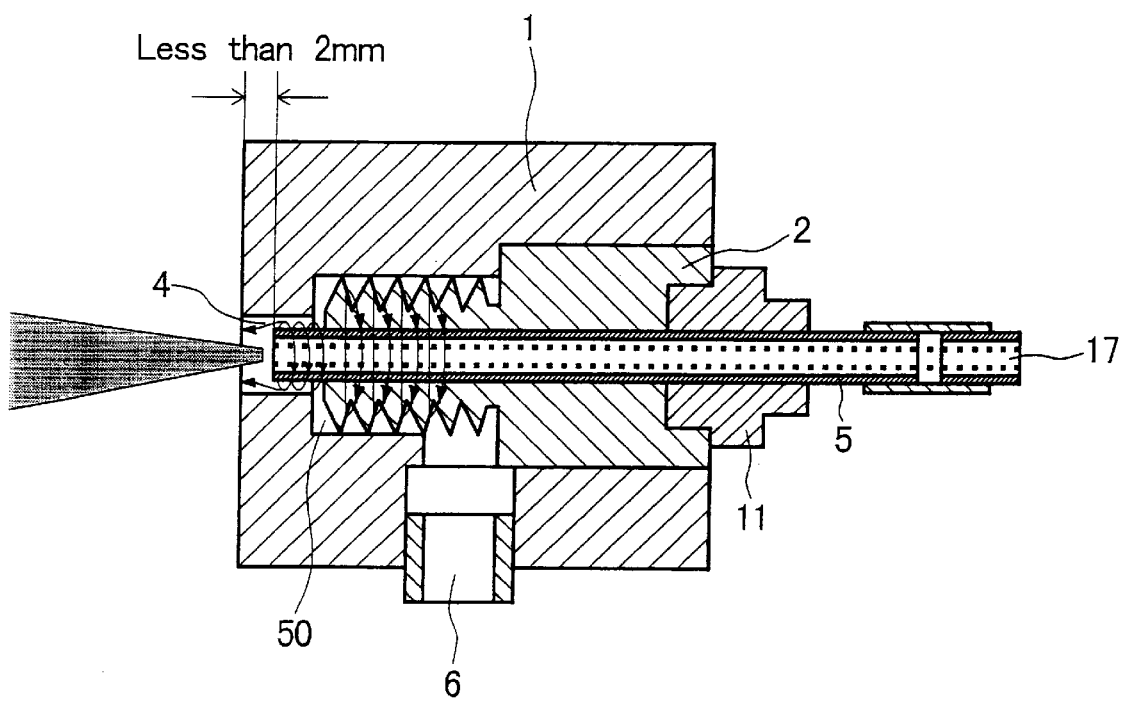
FIG. 21 is a cross-sectional illustration of a sonic spray nebulizer with a helical flow path for nebulizer gas.

FIG. 21 is a cross-sectional view of a supersonic array nebulizer based on a further embodiment of the present invention. A spray gas is introduced through a gas inlet 6 and circulated by a helical gas path. Further, the spray gas is injected from an orifice 4 and reaches a supersonic speed of Mach 1 or more. A sample solution delivered from an end of a tube 5 is sprayed by its supersonic gas flow. The distance between the end of the tube 5 and the outside of an orifice member is less than or equal to 2 mm. Thus, the surface of a liquid is torn off by the velocity of a gas lying in the direction of its injection without reflecting a shock wave of a supersonic gas flow to thereby produce fine droplets.

Embodiment 13

Figure 22:
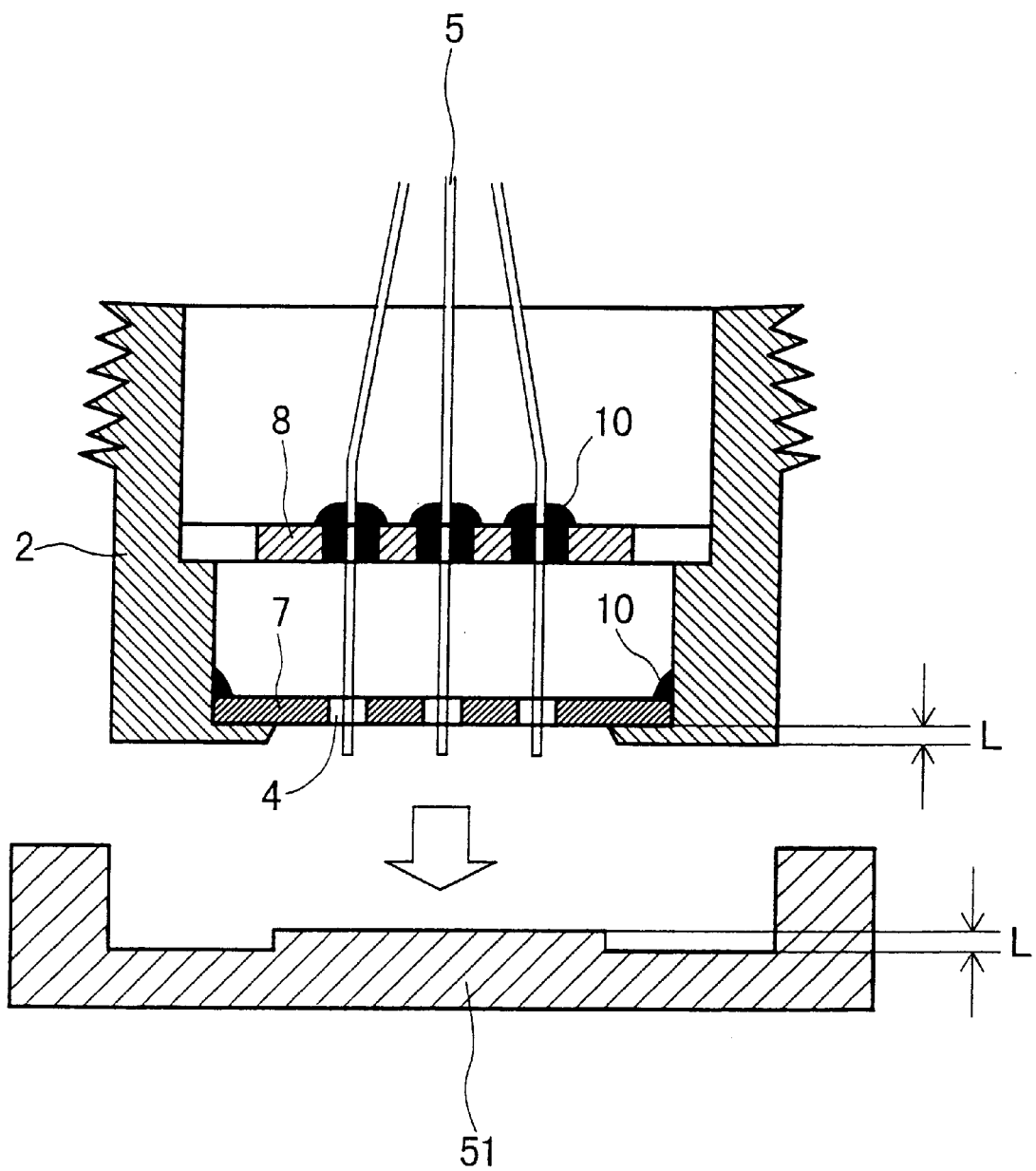
FIG. 22 is a pictorial illustration of the supersonic spray array nebulizer with a tool.

A method of assembling a supersonic array nebulizer based on a still further embodiment of the present invention is simply shown in FIG. 22. As shown in FIG. 1, the supersonic array nebulizer comprises the first member and the second member. As to an assembly procedure, the supersonic array nebulizer is assembled in accordance with a procedure for fixing each tube 5 to the second member and thereafter coupling it to the first member. In order to fix the position of the end of the tube 5 with respect to an outer surface of an orifice member 7 with satisfactory accuracy, a jig 51 is used in an assembly process. A cylinder having a height of L is provided in the center of the jig. A tip or leading end of the second member is inserted into the jig 51 without any clearance, and the surface of its leading end is brought into contact with the outer surface of the orifice member 7. As a result, the position of the end of each tube 5 can be brought into contact with the outer surface of the orifice member 7. When the end of the tube 5 is projected by a constant distance from the outer surface of the orifice member 7, the height of the cylinder of the jig 51 may be set smaller than L.

A specific assembly process using the jig 51 will be described below. The orifice member 7 is first fixed to the second member with an adhesive 10. Care is needed so as not to cause the leakage of a gas from a clearance or gap between the orifice member 7 and the second member. Next, a fixing plate 8 is fixed with the adhesive 10. Thereafter, the tube 5 are inserted into their corresponding orifices 4 and holes defined in the fixing plate 8, and hence the positions of the tube 5 are determined by the jig 51. Further, each tube 5 is fixed to the fixing plate 8 with the adhesive 10. Next, the tubes 5 are inserted into a fixing tube 9 fixed to the first member, and the adhesive is poured into clearances between the tubes 5 and the fixing tube 9, whereby the first member and the second member are coupled to each other with the screw 3 (see FIG. 1) If they are fixed with the screw 3 before the setting of the adhesive, then the tube 5 is hard to break, thus providing convenience. Finally, the adhesive is buried in the clearance defined between the fixing tube 9 provided outside the first member and each tube 5 to hermetically seal the clearance. Hermetically sealing even both ends of the fixing tube 9 with the adhesive is necessary to prevent a high-pressure gas from leaking.

In the present invention as described above in detail, the spraying of a liquid is efficiently performed using a gas flow lying in a supersonic region. According to an array nebulizer, a sample liquid is divided into a plurality of tubes (capillaries) and introduced therein. Further, the sample liquid is sprayed at ends of the respective tubes through the use of a supersonic gas flow with high spray efficiency. Owing to this function, a reduction in spray efficiency is controlled even in the case of the high flow rate of the liquid. Particularly when it is utilized as a nebulizer for a high-sensitivity analytical apparatus, the sensitivity of the apparatus greatly increases.

While the present invention has been described with reference to the illustrative embodiments, this description is not intended to be construed in a limiting sense. Various modifications of the illustrative embodiments, as well as other embodiments of the invention, will be apparent to those skilled in the art on reference to this description. It is therefore contemplated that the appended claims will cover any such modifications or embodiments as fall within the true scope of the invention.

What is claimed is:

1. A nebulizer, comprising:
   a first member and a second member which are forming a chamber;
   a plate having at least one orifice;
   a first aperture in said first member for gas inlet;
   a second aperture in said second member for fixing said plate;
   at least one tube for delivering a liquid; and
   a fixing tube for fixing said tube, wherein one end of said tube is placed in said orifice, a diameter of said second aperture is smaller than that of said chamber, and a compressed gas and said liquid flows together through said orifice at a supersonic speed.

2. A nebulizer according to claim 1, wherein said one end of said tube is placed at substantially an outside surface of said orifice.

3. A nebulizer according to claim 1, wherein the mach number of the gas flow at an outside surface of said plate ranges from 1 to 2.

4. A nebulizer according to claim 1, wherein said at least one tube is a plurality of tubes for respectively delivering the liquid to said orifice.

* * * * *